United States Patent
Oberkobusch et al.

(10) Patent No.: US 8,268,015 B2
(45) Date of Patent: Sep. 18, 2012

(54) METHOD FOR DECOLORIZING KERATIN-CONTAINING FIBERS

(75) Inventors: Doris Oberkobusch, Duesseldorf (DE); Wibke Gross, Hueckelhoven (DE); Laura Stephan, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/161,612

(22) Filed: Jun. 16, 2011

(65) Prior Publication Data

US 2011/0247644 A1    Oct. 13, 2011

Related U.S. Application Data

(63) Continuation of application No. PCT/EP2009/066044, filed on Nov. 30, 2009.

(30) Foreign Application Priority Data

Dec. 16, 2008 (DE) .......................... 10 2008 062 239

(51) Int. Cl.
*A61Q 5/10* (2006.01)

(52) U.S. Cl. ............. 8/405; 8/565; 8/567; 8/568; 8/570; 8/572; 132/202; 132/208

(58) Field of Classification Search ............... 8/405, 565, 8/567, 568, 570, 572; 132/202, 208
See application file for complete search history.

(56) References Cited

U.S. PATENT DOCUMENTS

| | | | |
|---|---|---|---|
| 4,122,029 A | 10/1978 | Gee et al. | |
| 4,265,878 A | 5/1981 | Keil | |
| 4,324,780 A | 4/1982 | Jacquet et al. | |
| 4,393,886 A | 7/1983 | Strasilla et al. | |
| 4,421,769 A | 12/1983 | Dixon et al. | |
| 4,814,101 A | 3/1989 | Schieferstein et al. | |
| 4,865,774 A | 9/1989 | Fabrey et al. | |
| 4,931,218 A | 6/1990 | Schenker et al. | |
| 4,994,088 A | 2/1991 | Ando et al. | |
| 5,294,726 A | 3/1994 | Behler et al. | |
| 5,318,733 A | 6/1994 | Carduck et al. | |
| 5,998,537 A | 12/1999 | Good et al. | |
| 6,740,128 B2 | 5/2004 | Javet et al. | |
| 7,105,032 B2 | 9/2006 | Gross et al. | |
| 7,413,579 B2 | 8/2008 | Seiler et al. | |
| 2005/0262647 A1* | 12/2005 | Hoeffkes et al. | ................ 8/405 |

FOREIGN PATENT DOCUMENTS

| | | |
|---|---|---|
| CA | 2066226 A1 | 3/1991 |
| DE | 4440625 A1 | 5/1996 |
| DE | 19503465 A1 | 8/1996 |
| DE | 102007047685 A1 | 7/2008 |
| EP | 0874017 A2 | 10/1998 |
| EP | 0998908 A2 | 5/2000 |
| GB | 2066659 A | 7/1981 |
| GB | 2104091 A | 3/1983 |
| WO | 2005120445 A2 | 12/2005 |

OTHER PUBLICATIONS

STIC Search Report dated Apr. 26, 2012.*
"2.9.8 Breaking Strength of Tablets" Europäisches Arzneibuch, vol. 3. Ausgabe, 1997, pp. 143-144.

* cited by examiner

*Primary Examiner* — Eisa Elhilo

(57) ABSTRACT

Use of a composition comprising hydrogen peroxide in a cosmetic vehicle allows gentle discoloring of permanently colored, keratinous fibers which have been colored with a specific coloring composition. The coloring composition used for coloring the fibers comprises, in a cosmetic vehicle, a combination of at least one CH-acidic compound with at least one reactive carbonyl compound. The discoloring composition contains preferably between 0% and 15% by weight of hydrogen peroxide and has the effect, in particular in a working time of 5 to 20 minutes even without the use of organic peroxo compounds and in the absence of inorganic persalts, of effective color removal with simultaneous gentle treatment of the fibers.

12 Claims, No Drawings

METHOD FOR DECOLORIZING KERATIN-CONTAINING FIBERS

CROSS REFERENCE TO RELATED APPLICATIONS

The present application is a continuation of International Application No. PCT/EP2009/066044 filed 30 Nov. 2009, which claims priority to German Patent Application No. 10 2008 062 239.7 filed 16 Dec. 2008, both of which are incorporated herein by reference.

The present invention relates to the use of a decolorizing agent containing hydrogen peroxide in a cosmetic carrier for decolorizing dyed keratin-containing fibers which have been dyed with a ready-to-use dyeing agent containing a combination of at least one CH-acidic compound with at least one reactive carbonyl compound in a cosmetic carrier. The invention furthermore provides a corresponding decolorizing method and a kit containing both the specific dyeing agent and the decolorizing agent.

Various dyeing systems for dyeing hair are known to a person skilled in the art, which differ greatly in terms of the permanency of the color on the hair and the degree of damage to which the hair is subjected during the hair dyeing process.

"Oxidation dyeing agents" are used for permanent, high intensity dyed colors with corresponding fastness characteristics. Such dyeing agents conventionally contain oxidation dye intermediates (i.e., "developer components" and "coupler components"). Under the influence of oxidation agents or atmospheric oxygen, the developer components develop the actual dyes through action with one another or through coupling with one or more coupler components. Oxidation dyeing agents provide excellent, long-lasting dyeing results. A mixture of a relatively large number of oxidation dye precursors must, however, normally be used if natural looking dyed colors are to be obtained. Often, direct dyes are additionally used for shading purposes.

The developer components used are typically primary aromatic amines with a further free or substituted hydroxyl or amino group located in para or ortho position, heterocyclic hydrazones, diaminopyrazole derivatives and 2,4,5,6-tetraaminopyrimidine and the derivatives thereof.

Particular representatives include p-phenylenediamine, p-tolylenediamine, 2,4,5,6-tetraaminopyrimidine, p-aminophenol, N,N-bis(2-hydroxyethyl)-phenylenediamine, 2-(2,5-diaminophenyl)ethanol, 2-(2,5-diaminophenoxy) ethanol, 4-amino-3-methylphenol, 2-aminomethyl-4-aminophenol, 4,5-diamino-1-(2-hydroxyethyl)pyrazole, 2-hydroxy-4,5,6-triaminopyrimidine, 2,4-dihydroxy-5,6-diaminopyrimidine, 2,5,6-triamino-4-hydroxypyrimidine and N,N'-bis(2-hydroxyethyl)-N,N'-bis(4-aminophenyl)-1,3-diaminopropan-2-ol.

Coupler components typically used include m-phenylenediamine derivatives, naphthols, pyridine derivatives, resorcinol and resorcinol derivatives, pyrazolones and m-aminophenols. Particularly suitable coupler substances are 1-naphthol, 1,5-dihydroxynaphthalene, 2,7-dihydroxynaphthalene, 1,7-dihydroxynaphthalene, 5-amino-2-methylphenol, m-aminophenol, resorcinol, resorcinol monomethyl ether, m-phenylenediamine, 1-phenyl-3-methylpyrazol-5-one, 2,4-dichloro-3-aminophenol, 1,3-bis-(2,4-diaminophenoxy) propane, 2-amino-3-hydroxypyridine, 4-chlororesorcinol, 2-chloro-6-methyl-3-aminophenol, 2-methylresorcinol, 5-methylresorcinol and 2-methyl-4-chloro-5-aminophenol.

For temporary dyeing, dyes or tints having "direct" dyes as the coloring component are typically used. These are dye molecules which key directly to the substrate and do not need an oxidative process to develop the color. These dyes include henna, which has been known since antiquity for dyeing bodies and hair. These dyed colors are in general distinctly more sensitive to shampooing than are oxidatively dyed colors, such that an often unwanted shift in shade or even a visible, uniform color loss occurs much more quickly.

Another color changing option involves using dyeing agents having "oxo dye intermediates". A first class of oxo dye intermediates comprises compounds with at least one reactive carbonyl group. This first class is designated component (oxo1). A second class of oxo dye intermediates is constituted by CH-acidic compounds and compounds with a primary or secondary amino group or hydroxyl group, which are in turn chosen from compounds of primary or secondary aromatic amines, nitrogenous heterocyclic compounds and aromatic hydroxyl compounds. This second class is designated component (oxo2). The above-stated components (oxo 1) and (oxo2) are in general not themselves dyes and are therefore not individually suitable for dyeing fibers containing keratin. In combination, they form dyes in a non-oxidative, "oxo dyeing" process. The resultant dyed colors are virtually permanent and predominantly have color fastness values on the keratin-containing fibers comparable with those of oxidation dyeing.

The range of shades achievable with this gentle oxo dyeing method is very wide and the resultant dyed colors often exhibit acceptable brightness and color depth. Among the (oxo2) component compounds, however, corresponding oxidation dye intermediates of the developer and/or coupler type may be used with or without the involvement of an oxidation agent. The oxo dyeing method may thus be straightforwardly combined with the oxidative dyeing system.

Since bright colors with good permanency on hair may be achieved in oxo dyeing even without using oxidizing agents such as hydrogen peroxide, this dyeing method is associated with slight hair damage and, given this background, is of particular interest to the consumer.

WO 2004/022016 A1 and WO 2005/120445 A2, for example, disclose the technical implementation of oxo dyeing.

DE 10022743 A1 describes an agent for dyeing hair which is produced by mixing a component (A1) containing an enamine or the acid addition salt thereof and a component (A2) containing a carbonyl compound and a primary amine. Component A1 has an acidic pH value, while component A2 has an alkaline pH value.

In addition to coloring, the stripping of dyes is another technical field of importance. This is generally taken to mean the removal of dyed colors by washing out, chemical modification or destruction of the dye. Oxidative or reductive decolorization of dyed materials is in particular used in the decolorization of textiles or hair.

Oxidative decolorization usually provides good results. However, the strong oxidizing action of the oxidizing agent used for decolorization may chemically modify the structure of the substrate. This is accompanied by an unwanted physical modification of the substrate. Hair may, for example, become brittle or, in particular in the case of repeated decolorization, even break. Visual appearance and tactile properties, as well as the durability of the substrate are impaired as a result.

Using hydrogen peroxide as the sole oxidizing agent is not sufficient for successful color stripping of permanent oxidation dyed colors. As is known, a person skilled in the art uses cosmetic decolorizing agents for stripping the color from permanent oxidation dyed colors. Such decolorizing agents, in addition to hydrogen peroxide, also contain either at least one organic peroxo compound (such as organic peracids such as perphthalic acid, peracetic acid), or at least one inorganic per-salt (such as persulfate, perborate or peroxydisulfate salts). These decolorizing agents correspond, for example, to known blonding agents for ultrablonding hair The previously described physical substrate modifications of variable degrees of severity may be observed when ultrablonding agents with their strong oxidizing action have been used.

The present invention provides, for the purposes of oxo dyeing, a kit for dyeing and decolorizing keratin-containing fibers, which enables the consumer to carry out, in addition to permanent, gentle oxo dyeing, maximally complete, gentle color stripping. After color stripping, the keratin-containing fibers should have had their artificially applied oxo dyed color maximally removed, have suffered no or the least possible damage to their fiber structure and in particular exhibit a soft handle and good combability.

It has surprisingly now been found that hydrogen-containing decolorizing agents bring about excellent color stripping of keratin-containing fibers dyed by oxo dyeing while simultaneously being gentle on the fibers. It is here possible to dispense with the use of organic peroxo compounds and inorganic per-salts. Gentle decolorization of permanent oxo dyeing is moreover successful when just small quantities of hydrogen peroxide are used.

The present invention accordingly firstly provides a kit (packaging unit) for dyeing and decolorizing keratin-containing fibers, in particular human hair, comprising:
  at least one cosmetic multicomponent dyeing agent comprising at least one cosmetic agent A1 and at least one cosmetic agent A2,
  at least one cosmetic decolorizing agent B containing hydrogen peroxide in a cosmetic carrier, and
  optionally, at least one set of instructions,
wherein
  at least one agent A1 and at least one agent A2 are mixed to yield a ready-to-use dyeing agent for dyeing keratin-containing fibers, and
  keratin-containing fibers dyed with the ready-to-use dyeing agent are, if required, decolorized with the decolorizing agent B, and
  the ready-to-use dyeing agent contains at least one CH-acidic compound and at least one reactive carbonyl compound in a cosmetic carrier,
with the proviso that agents A1, A2 and B are each present in separately formulated form.

Keratin-containing fibers here refer to wool, furs, feathers and in particular human hair. Dyeing agents according to the invention may, however, also be used for dyeing other natural fibers such as cotton, jute, sisal, linen or silk, modified natural fibers, such as regenerated cellulose, nitro-, alkyl- or hydroxyalkyl- or acetylcellulose and synthetic fibers, such as polyamide, polyacrylonitrile, polyurethane and polyester fibers.

For the purposes of the invention, "separately formulated" means that the agents in question are each formulated in their own container. Various types of packaging may be used as containers, such as films, pouches, bottles, cans, aerosol containers. A chamber of a multichamber container is also considered to be a container.

For the purposes of the invention, decolorizing means color stripping of the dyed colors obtained by the ready-to-use dyeing agents of the kit while largely obtaining the natural color of the keratin-containing fibers or the natural hair color.

The kit according to the invention constitutes an effective and gentle dyeing and decolorizing system. For the purposes of the above-described kit, the invention consequently provides that
  for dyeing keratin-containing fibers, at least one agent A1 and at least one agent A2 are mixed to yield a ready-to-use dyeing agent and
  the keratin-containing fibers dyed with the ready-to-use dyeing agent are, if required, decolorized with the decolorizing agent B.

For the purposes of a preferred embodiment, the kit therefore additionally contains instructions for use, which inter alia instruct that
  for dyeing keratin-containing fibers, at least one agent A1 and at least one agent A2 are mixed to yield a ready-to-use dyeing agent, and
  the keratin-containing fibers dyed with the ready-to-use dyeing agent are, if required, decolorized with the decolorizing agent B.

For the purposes of the invention, instructions for use are for example a notice on a separate information medium, optionally enclosed in the pack, for example the outer packaging, a brochure, a booklet, a package insert or a file on a data storage medium.

In a preferred embodiment of the kit according to the invention, the CH-acidic compounds and the reactive carbonyl compounds of the ready-to-use dyeing agent are formulated separately from one another and are present in at least one agent A1 and at least one agent A2, with the provisos that
  agent A1 contains at least one CH-acidic compound in a cosmetic carrier, and
  agent A2 contains at least one reactive carbonyl compound in a cosmetic carrier.

For the purposes of this embodiment, agent A1 thus contains no reactive carbonyl compounds and agent A2 contains no CH-acidic compounds. The ready-to-use dyeing agent—agent A1—contains at least one CH-acidic compound.

Compounds generally regarded as CH-acidic compounds are those having a hydrogen atom attached to an aliphatic carbon atom, activation of the corresponding carbon-hydrogen bond being brought about on the basis of electron-attracting substituents. The hydrogen atom can be abstracted with the assistance of a base. The ready-to-use dyeing agent preferably contains at least one CH-acidic compound chosen from at least one compound of formula (CH-1) and/or from at least one compound of formula (CH-2)

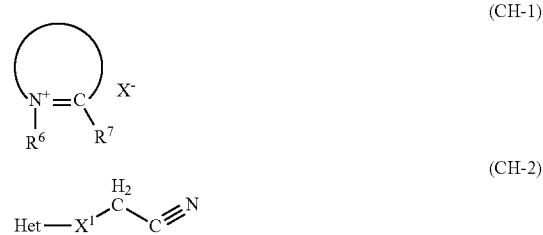

wherein
  $R^6$ is a linear or cyclic ($C_1$ to $C_6$) alkyl group, a ($C_2$ to $C_6$) alkenyl group, an optionally substituted aryl group, an optionally substituted heteroaryl group, an aryl-($C_1$ to $C_6$)-alkyl group, a ($C_1$ to $C_6$) hydroxyalkyl group, a ($C_2$ to $C_6$) polyhydroxyalkyl group, a ($C_1$ to $C_6$)-alkoxy-($C_1$ to $C_6$)-alkyl group, a group $R'R''N-(CH_2)_m-$, wherein $R'$ and $R''$ mutually independently are a hydrogen atom, a ($C_1$ to $C_4$) alkyl group, a ($C_1$ to $C_4$) hydroxyalkyl group or an aryl-($C_1$ to $C_6$)-alkyl group, $R^I$ and $R^{II}$, together with the nitrogen atom, being capable of forming a 5-, 6- or 7-membered ring and m is a number 2, 3, 4, 5 or 6, $R^7$ is a ($C_1$ to $C_6$) alkyl group, particularly a methyl group, $X^-$ is a physiologically acceptable anion, the cycle of formula (CH-1) represents any ring structures which may additionally contain further heteroatoms such as nitrogen, oxygen or sulfur and may furthermore bear fused ring structures, all these ring structures being capable of bearing additional substituents, Het is an optionally substituted heteroaromatic, and $X^1$ is a direct bond or a carbonyl group.

Compounds of formulae (CH-1) and (CH-2) are CH-acidic compounds. The corresponding uncharged enamine form may purposefully be prepared from cationic compounds of formula (CH-1) by addition of a base, which effects elimination of a proton. By way of example for compounds of formula (CH-1), the preparation of the enamine form is illustrated below with reference to formulae (CH-1-A) and (CH-1-B) with $R^7$=$CH_3$. The corresponding enamine forms of the CH-acidic compounds of formula (CH-1) are also according to the invention.

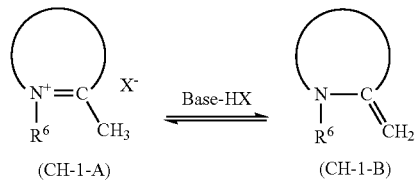

(CH-1-A)          (CH-1-B)

It is particularly preferred according to the invention to select compounds of formula (CH-1) from at least a compound of formula (CH-3)

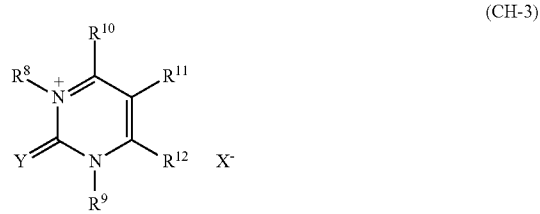

(CH-3)

wherein $R^8$ and $R^9$ mutually independently are a linear or cyclic ($C_1$ to $C_6$) alkyl group, a ($C_2$ to $C_6$) alkenyl group, an optionally substituted aryl group, an optionally substituted heteroaryl group, an aryl-($C_1$ to $C_6$)-alkyl group, a ($C_1$ to $C_6$) hydroxyalkyl group, a ($C_2$ to $C_6$) polyhydroxyalkyl group, a ($C_1$ to $C_6$)-alkoxy-($C_1$ to $C_6$)-alkyl group, a group $R^I R^{II} N$—$(CH_2)_m$—, wherein $R^I$ and $R^{II}$ mutually independently are a hydrogen atom, a ($C_1$ to $C_4$) alkyl group, a ($C_1$ to $C_4$) hydroxyalkyl group or an aryl-($C_1$ to $C_4$)-alkyl group, $R^I$ and $R^{II}$, together with the nitrogen atom, capable of forming a 5-, 6- or 7-membered ring, and m is 2, 3, 4, 5 or 6, $R^{10}$ and $R^{12}$ mutually independently are a hydrogen atom or a $C_1$-$C_6$ alkyl group, at least one of residues $R^{10}$ and $R^{12}$ being a $C_1$-$C_6$ alkyl group, $R^{11}$ is a hydrogen atom, a ($C_1$ to $C_6$) alkyl group, a ($C_1$ to $C_6$) hydroxyalkyl group, a ($C_2$ to $C_6$) polyhydroxyalkyl group, a ($C_1$ to $C_6$) alkoxy group, a ($C_1$ to $C_6$) hydroxyalkoxy group, a group $R^{III} R^{IV} N$—$(CH_2)_q$—, wherein $R^{III}$ and $R^{IV}$ mutually independently are a hydrogen atom, a ($C_1$ to $C_6$) alkyl group, a ($C_1$-$C_6$) hydroxyalkyl group or an aryl-($C_1$-$C_6$)-alkyl group, and q is 1, 2, 3, 4, 5 or 6, residue $R^{11}$ capable of forming together with one of residues $R^{10}$ or $R^{12}$ a 5- or 6-membered aromatic ring, which may optionally be substituted with a halogen atom, a ($C_1$ to $C_6$) alkyl group, a ($C_1$ to $C_6$) hydroxyalkyl group, a ($C_2$ to $C_6$) polyhydroxyalkyl group, a ($C_1$ to $C_6$) alkoxy group, a ($C_1$ to $C_6$) hydroxyalkoxy group, a nitro group, a hydroxy group, a group $R^V R^{VI} N$—$(CH_2)_s$—, wherein $R^V$ and $R^{VI}$ mutually independently are a hydrogen atom, a ($C_1$ to $C_6$) alkyl group, a ($C_1$ to $C_6$) hydroxyalkyl group or an aryl-($C_1$ to $C_6$)-alkyl group, and s is 0, 1, 2, 3, 4, 5 or 6;

Y is an oxygen atom, a sulfur atom or a group $NR^{VII}$, wherein $R^{VII}$ is a hydrogen atom, an aryl group, a heteroaryl group, a ($C_1$ to $C_6$) alkyl group or an aryl-($C_1$-$C_6$)-alkyl group; and $X^-$ is a physiologically acceptable anion.

At least one group $R^{10}$ or $R^{12}$ of formula (CH-3) is a ($C_1$ to $C_6$) alkyl group. This alkyl group preferably bears at least two hydrogen atoms on its α-carbon atom. Particularly preferred alkyl groups are the methyl, ethyl, propyl, n-butyl, iso-butyl, n-pentyl, neopentyl, n-hexyl group. $R^{10}$ and $R^{12}$ very particularly preferably mutually independently represent hydrogen or a methyl group, at least one group $R^{10}$ or $R^{12}$ being a methyl group.

In a preferred embodiment, Y of formula (CH-3) is an oxygen or sulfur atom, preferably an oxygen atom.

$R^8$ of formula (CH-3) is preferably chosen from a ($C_1$ to $C_6$) alkyl group (preferably a methyl group), a ($C_2$ to $C_6$) alkenyl group (particularly an allyl group), a ($C_2$ to $C_6$) hydroxyalkyl group (particularly a 2-hydroxyethyl group), or an optionally substituted benzyl group.

$R^{11}$ of formula (CH-3) preferably is a hydrogen atom.

In formula (CH-3), $R^9$, $R^{10}$ and $R^{12}$ are preferably a methyl group, $R^{11}$ is a hydrogen atom, Y an oxygen or sulfur atom, and $R^8$ is chosen from a ($C_1$ to $C_6$) alkyl group (preferably a methyl group), a ($C_2$ to $C_6$) alkenyl group (particularly an allyl group), a ($C_2$ to $C_6$) hydroxyalkyl group (particularly a 2-hydroxyethyl group), or an optionally substituted benzyl group.

Very particularly bright dyed hair colors may be obtained if the CH-acidic compound of formula (CH-1) and/or of formula (CH-2) present in ready-to-use dyeing agents is a compound chosen from at least one compound of 2-(2-furoyl)-acetonitrile, 2-(5-bromo-2-furoyl)-acetonitrile, 3-(2,5-dimethyl-3-furyl)-3-oxopropanenitrile, 2-(2-thenyl)-acetonitrile, 2-(3-thenoyl)-acetonitrile, 2-(5-fluoro-2-thenyl)-acetonitrile, 2-(5-chloro-2-thenyl)-acetonitrile, 2-(5-bromo-2-thenoyl)-acetonitrile, 2-(5-methyl-2-thenyl)-acetonitrile, 2-(2,5-dimethylpyrrol-3-oyl)-acetonitrile, 2-(1, 2,5-trimethylpyrrol-3-oyl)-acetonitrile, 1H-benzimidazol-2-ylacetonitrile, 1H-benzothiazol-2-ylacetonitrile, 2-(pyrid-2-yl)-acetonitrile, 2,6-bis(cyanomethyl)-pyridine, 2-(indol-3-oyl)-acetonitrile, 2-(2-methylindol-3-oyl)-acetonitrile, 2-(6-hydroxy-4,7-dimethoxy-1-benzofuran-5-oyl)-acetonitrile and the salts with a physiologically acceptable counterion $X^-$ of 1,2-dihydro-1,3,4,6-tetramethyl-2-oxopyrimidinium, 1,2-dihydro-1,3-diethyl-4,6-dimethyl-2-oxopyrimidinium, 1,2-dihydro-1,3-dipropyl-4,6-dimethyl-2-oxopyrimidinium, 1,2-dihydro-1,3-di(2-hydroxyethyl)-4,6-dimethyl-2-oxopyrimidinium, 1,2-dihydro-1,3-diphenyl-4,6-dimethyl-2-oxopyrimidinium, 1,2-dihydro-1,3,4-trimethyl-2-oxopyrimidinium, 1,2-dihydro-1,3-diethyl-4-methyl-2- oxopyrimidinium, 1,2-dihydro-1,3-dipropyl-4-methyl-2-oxopyrimidinium, 1,2-dihydro-1,3-di(2-hydroxyethyl)-4-methyl-2-oxopyrimidinium, 1,2-dihydro-1,3-diphenyl-4-methyl-2-oxopyrimidinium, 1-allyl-1,2-dihydro-3,4,6-trimethyl-2-oxopyrimidinium, 1,2-dihydro-1-(2-hydroxyethyl)-3,4,6-trimethyl-2-oxopyrimidinium, 1,2-dihydro-1,3,4,6-tetramethyl-2-thioxopyrimidinium, 1,2-dihydro-1,3-diethyl-4,6-dimethyl-2-thioxopyrimidinium, 1,2-dihydro-1,3-dipropyl-4,6-dimethyl-2-thioxopyrimidinium, 1,2-dihydro-1,3-di(2-hydroxyethyl)-4,6-dimethyl-2-thioxopyrimidinium, 1,2-dihydro-1,3-diphenyl-4,6-dimethyl-2-thioxopyrimidinium, 1,2-dihydro-1,3,4-trimethyl-2-thioxopyrimidinium, 1,2-dihydro-1,3-diethyl-4-methyl-2-thioxopyrimidinium, 1,2-dihydro-1,3-dipropyl-4-methyl-2-thioxopyrimidinium, 1,2-dihydro-1,3-di(2-hydroxyethyl)-4-methyl-2-thioxopyrimidinium, 1,2-dihydro-1,3-diphenyl-4-methyl-2-thioxopyrimidinium, 1,2-dihydro-3,4-dimethyl-2-oxoquinazolinium and 1,2-dihydro-3,4-dimethyl-2-thioxoquinazolinium. Compounds of this group are therefore particularly preferred.

The ready-to-use dyeing agent—agent A2—contains at least one reactive carbonyl compound.

For the purposes of the invention, reactive carbonyl compounds have at least one carbonyl group as reactive group which reacts with the CH-acidic component to form a covalent bond. Preferred reactive carbonyl compounds are chosen from compounds which bear at least one formyl group and/or at least one keto group, particularly at least one formyl group. According to the invention, compounds which may be used as component (Oxo1) are also those in which the reactive carbonyl group is derivatized or masked so that the reactivity of the carbon atom of the derivatized carbonyl group towards component (Oxo2) is always present. These derivatives are preferably addition compounds of—
a) amines and the derivatives thereof resulting in the formation of imines or oximes as an addition compound;
b) alcohols resulting in the formation of acetals or ketals as an addition compound; and/or
c) water resulting in the formation of hydrates as an addition compound (component (Oxo1) is derived in this case c) from an aldehyde)
onto the carbon atom of carbonyl group of the reactive carbonyl compound.

Preferred reactive carbonyl compounds are chosen from benzaldehyde and the derivatives thereof, naphthaldehyde and the derivatives thereof, cinnamaldehyde and the derivatives thereof, 2-formylmethylene-1,3,3-trimethylindoline (Fischer's aldehyde or tribasic aldehyde), 2-indolealdehyde, 3-indolealdehyde, 1-methylindole-3-aldehyde, 2-methylindole-3-aldehyde, 2-(1',3',3'-trimethyl-2-indolinylidene)-acetaldehyde, 1-methylpyrrole-2-aldehyde, pyridoxal, 2,3-dihydro-1,5-dimethyl-3-oxo-2-phenyl-1H-pyrazole-4-carboxaldehyde, furfural, 5-nitrofurfural, chromone-3-aldehyde, 3-(5'-nitro-2'-furyl)-acrolein, 3-(2'-furyl)-acrolein and imidazole-2-aldehyde, 5-(4-dimethylaminophenyl)penta-2,4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 5-(4-dimethylamino-1-naphthyl)penta-3,5-dienal, piperonal, 6-nitropiperonal, 2-nitropiperonal, 5-nitrovanillin, 2,5-dinitrosalicylaldehyde, 5-bromo-3-nitrosalicylaldehyde, 3-nitro-4-formylbenzenesulfonic acid, 4-formyl-1-methylpyridinium, 2-formyl-1-methylpyridinium, 4-formyl-1-ethylpyridinium, 2-formyl-1-ethylpyridinium, 4-formyl-1-benzylpyridinium, 2-formyl-1-benzylpyridinium, 4-formyl-1,2-dimethylpyridinium, 4-formyl-1,3-dimethylpyridinium, 4-formyl-1-methylquinolinium, 2-formyl-1-methylquinolinium, 5-formyl-1-methylquinolinium, 6-formyl-1-methylquinolinium, 7-formyl-1-methylquinolinium, 8-formyl-1-methylquinolinium, 5-formyl-1-ethylquinolinium, 6-formyl-1-ethylquinolinium, 7-formyl-1-ethylquinolinium, 8-formyl-1-ethylquinolinium, 5-formyl-1-benzylquinolinium, 6-formyl-1-benzylquinolinium, 7-formyl-1-benzylquinolinium, 8-formyl-1-benzylquinolinium, 5-formyl-1-allylquinolinium, 6-formyl-1-allylquinolinium, 7-formyl-1-allylquinolinium and 8-formyl-1-allylquinolinium benzenesulfonate, p-toluenesulfonate, methanesulfonate, perchlorate, sulfate, chloride, bromide, iodide, tetrachlorozincate, methylsulfate, trifluoromethanesulfonate, tetrafluoroborate, isatin, 1-methylisatin, 1-allylisatin, 1-hydroxymethylisatin, 5-chloroisatin, 5-methoxyisatin, 5-nitroisatin, 6-nitroisatin, 5-sulfoisatin, 5-carboxyisatin, quinisatin, 1-methylquinisatin, as well as any desired mixtures of the above-stated compounds.

It is particularly preferred if the reactive carbonyl compound used is a compound chosen from 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde, 4-dimethylamino-2-methoxybenzaldehyde, 2-methoxy-benzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxy-benzaldehyde, 2,3-dihydroxybenzaldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-dihydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methylbenzaldehyde, 3,4-dihydroxy-5-methylbenzaldehyde, 3,4-dihydroxy-6-methylbenzaldehyde, 3,4-dihydroxy-2-methoxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-dimethylaminobenzaldehyde, 4-diethylaminobenzaldehyde, 4-dimethylamino-2-hydroxybenzaldehyde, 4-pynolidinobenzaldehyde, 4-morpholinobenzaldehyde, 2-morpholinobenzaldehyde, 4-piperidinobenzaldehyde, 3,5-dichloro-4-hydroxybenzaldehyde, 4-hydroxy-3,5-diiodobenzaldehyde, 3-chloro-4-hydroxybenzaldehyde, 5-chloro-3,4-dihydroxybenzaldehyde, 5-bromo-3,4-dihydroxybenzaldehyde, 3-chloro-4-hydroxy-5-methoxybenzaldehyde, 4-hydroxy-3-iodo-5-methoxybenzaldehyde, 2-methoxy-1-naphthaldehyde, 4-methoxy-1-naphthaldehyde, 2-hydroxy-1-naphthaldehyde, 2,4-dihydroxynaphthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-dimethylamino-1-naphthaldehyde, 3-hydroxy-4-nitrobenzaldehyde, 2-hydroxy-3-methoxy-5-nitrobenzaldehyde, 5-nitrovanillin, 2,5-dinitrosalicylaldehyde, 5-bromo-3-nitrosalicylaldehyde, 2-dimethylamino-benzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 3-carboxy-4-hydroxybenzaldehyde, 5-carboxyvanillin, 3-carboxy-4-hydroxy-5-methylbenzaldehyde, 3-carboxy-5-ethoxy-4-hydroxybenzaldehyde, 3-carboxy-4-hydroxybenzaldehyde, 5-carboxyvanillin, 3-carboxy-4-hydroxy-5-methylbenzaldehyde, 3-carboxy-5-ethoxy-4-hydroxybenzaldehyde, 3-allyl-4-hydroxybenzaldehyde, 3-allyl-4-hydroxy-5-methoxybenzaldehyde, 3-allyl-4-hydroxy-5-methylbenzaldehyde, 3-allyl-5-bromo-4-hydroxybenzaldehyde, 3,5-diallyl-4-hydroxybenzaldehyde, 3-allyl-5-carboxy-4-hydroxybenzaldehyde (3-allyl-5-formyl-2-hydroxybenzoic acid), 3-allyl-4-hydroxy-5-formylbenzaldehyde, (5-allyl-4-hydroxyisophthalaldehyde), 2,3-dihydro-1,5-dimethyl-3-oxo-2-phenyl-1H-pyrazole-4-carboxaldehyde or mixtures thereof.

Reactive carbonyl compounds are preferably used in a quantity of 0.03 to 65.00 mmol, relative to 100 g of the ready-to-use dyeing agent. It is particularly preferred to use 1.00 to 30.00 mmol, relative to 100 g of the ready-to-use dyeing agent.

CH-acidic compounds of formula (CH-1) and/or of formula (CH-2) in the ready-to-use dyeing agent are preferably used in a quantity of 0.03 to 65.00 mmol, relative to 100 g of the ready-to-use dyeing agent. It is particularly preferred to use 1.00 to 30.00 mmol, relative to 100 g of the ready-to-use dyeing agent.

In one embodiment, agents A1 and A2 may be present in the kit in pulverulent or granular form or as moldings.

A pulverulent agent A1 or A2 has a preferred average particle size of 0.0001 to 50 μm, particularly 0.05 to 30 μm.

According to the invention, granules mean granular particles. These granular particles are flowable.

Granules may be produced by wet granulation, by dry granulation or compaction and by melt solidification granulation. The most usual granulation technique is wet granulation, since this technique is subject to the least restrictions and most reliably gives rise to granules with favorable characteristics. Wet granulation proceeds by moistening the powder mixture with solvents and/or solvent mixtures and/or solutions of binders and/or solutions of adhesives and is preferably carried out in mixers, fluidized beds or spray towers, it being possible for said mixers to be equipped, for example, with stirring and kneading tools. Combinations of fluidized bed(s) and mixer(s), or combinations of different mixers may, however, also be used for granulation. Granulation proceeds under the action of low to elevated shear forces.

If agents A1 or A2 are present in the form of moldings, these moldings according to the invention may be of any geometric shape, such as for example concave, convex, biconcave, biconvex, cubic, tetragonal, orthorhombic, cylindrical, spherical, cylinder segment-shaped, disk-shaped, tetrahedral, dodecahedral, octahedral, conical, pyramidal, ellipsoidal, pent-, hept- and octagonally prismatic and rhombohedral shapes. Completely irregular base areas such as arrow or animal shapes, trees, clouds etc. may also be created. Configuration as a plate, rod or bar shape, cube, cuboid and corresponding three-dimensional elements with planar side faces and in particular cylindrical developments with a circular or oval cross-section and moldings with a spherical geometry are preferred according to the invention. Moldings in a morphology with spherical geometry are particularly preferred.

A cylindrical development here includes presentations ranging from a tablet up to compact cylinder pieces with a ratio of height to diameter of greater than 1. If the base molding has corners and edges, these are preferably rounded. An embodiment with rounded corners and bevelled ("chamfered") edges is preferred as an additional visual differentiation.

In addition to a spherical morphology, the spherical development also comprises a hybrid spherical and cylindrical shape, each base face of the cylinder being capped with a hemisphere. The hemispheres preferably have a radius of approx. 4 mm and the entire molding of this development has a length of 12-14 mm.

A molding according to the invention with a spherical development may be produced using known methods, it being possible to produce the molding by extruding a premix with subsequent shaping.

For the purposes of a preferred embodiment, agents A1 and/or A2 formulated as solids contain at least one alkalizing agent.

These alkalizing agents are preferably chosen from at least one alkalizing agent from basic amino acids, alkali metal hydroxides, alkanolamines, alkali metal metasilicates, urea, morpholine, N-methylglucamine, imidazole, alkali metal phosphates and alkali metal hydrogenphosphates. Preferably used alkali metal ions are lithium, sodium, potassium, in particular sodium or potassium.

Basic amino acids usable as an alkalizing agent according to the invention are preferably chosen from L-arginine, D-arginine, D,L-arginine, L-histidine, D-histidine, D,L-histidine, L-lysine, D-lysine, D,L-lysine. Particularly preferably L-arginine, D-arginine, and/or D,L-arginine are used as an alkalizing agent for the purposes of the invention.

Alkali metal hydroxides usable as an alkalizing agent according to the invention are preferably chosen from sodium hydroxide and potassium hydroxide.

Alkanolamines usable as an alkalizing agent according to the invention are preferably chosen from primary amines with a $C_2$-$C_6$ alkyl parent substance having at least one hydroxyl group. Particularly preferred alkanolamines are chosen from 2-aminoethan-1-ol(monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Alkanolamines which are very particularly preferred according to the invention are chosen from 2-aminoethan-1-ol, 2-amino-2-methylpropan-1-ol and 2-amino-2-methylpropane-1,3-diol.

The alkalizing agent is particularly preferably chosen from 2-aminoethanol, 2-amino-2-methylpropan-1-ol, 2-amino-2- methylpropane-1,3-diol, potassium hydroxide, sodium hydroxide, L-arginine, D-arginine, DL-arginine, N-methylglucamine, morpholine, imidazole and urea.

When agents A1 and A2 are in solid form, alkalizing agents which are present in solid form are particularly preferred.

Agents A1 and A2 in powder, granule or molding form are then jointly mixed in a liquid cosmetic agent A3 or in water to obtain the ready-to-use dyeing agent. The liquid cosmetic agent A3 can also be included in the kit according to the invention.

Suitable liquid cosmetic carriers for the agent A3 are in particular creams, emulsions, gels or also surfactant-containing foaming solutions, such as shampoos, foam aerosols or other preparations suitable for use on the hair. The liquid cosmetic carriers may in particular be aqueous or aqueous-alcoholic.

According to the invention, liquid means that the cosmetic carrier has liquid state of matter at 25° C. under a pressure of 1 atm.

An aqueous cosmetic carrier contains at least 50 wt. % water.

For the purposes of the present invention, aqueous-alcoholic cosmetic carriers are aqueous solutions containing 3 to 70 wt. % of an alcohol.

It is preferred according to the invention for the agent A3 additionally to contain at least one organic solvent. This organic solvent is in turn preferably chosen from ($C_1$ to $C_4$) monohydroxy alcohols,
($C_3$ to $C_6$) dihydroxy alcohols,
($C_3$ to $C_6$) trihydroxy alcohols,
cyclic, organic carbonates, and
compounds of formula H—(O—$CH_2CH_2$)$_n$—OR with R=hydrogen atom, methyl group and n=1, 2, 3 or 4.

Ethanol and isopropanol are regarded as preferred ($C_1$ to $C_4$) monohydroxy alcohols. 1,2-Propanediol is regarded as a preferred ($C_3$ to $C_6$) dihydroxy alcohol. Glycerol is regarded as a preferred ($C_3$ to $C_6$) trihydroxy alcohol.

At least one cyclic carbonic acid ester is preferably suitable according to the invention as a cyclic, organic carbonate. These cyclic esters of carbonic acid are derived from 1,3-dioxolan-2-one and may be described by the following parent structure of formula (I-1):

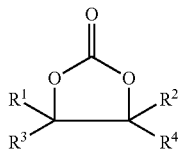

(I-1)

wherein residues $R^1$, $R^2$, $R^3$ and $R^4$ mutually independently are a hydrogen atom or organic residues, particularly alkyl, alkenyl or alkylaryl, which may additionally be substituted with further groups, particularly hydroxyl groups.

In the parent substance, 1,3-dioxolan-2-one, $R^1$, $R^2$, $R^3$ and $R^4$ of formula (I-1) are each a hydrogen atom. Further preferably suitable cyclic carbonic acid esters are derivatives of this parent substance, at least one of the residues $R^1$, $R^2$, $R^3$ and $R^4$ of formula (I-1) differing from a hydrogen atom. No boundaries are here set with regard to structural diversity, such that mono-, di-, tri- and tetra-substituted 1,3-dioxolan-2-ones of formula (I-1) are suitable for use for the purposes of the present invention.

In addition to the unsubstituted 1,3-dioxolan-2-one, derivatives of formula (I-2) below which are monosubstituted in position 4 are particularly preferred

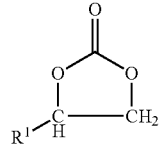

(I-2)

wherein $R^1$ is a substituted or unsubstituted alkyl, alkenyl or alkylaryl residue.

Preferred residues $R^1$ of formula (I-2) are methyl, ethyl, n-propyl, iso-propyl, and hydroxymethyl, 1-hydroxyethyl and 2-hydroxyethyl residues.

Particularly preferred agents according to the invention contain as 1,3-dioxolan-2-one derivative at least one compound of the above formula (I-2), wherein $R^1$ is a substituted or unsubstituted alkyl, alkenyl or alkylaryl residue, while in further preferred agents according to the invention residue $R^1$ in formula (I-2) is chosen from methyl, ethyl, n-propyl, iso-propyl and hydroxymethyl, 1-hydroxyethyl and 2-hydroxyethyl residues.

Particularly preferred 1,3-dioxolan-2-ones of formula (I-1) originate from the group of ethylene carbonate ($R^1$, $R^2$, $R^3$ and $R^4$=H), propylene carbonate ($R^1$=$CH_3$ and $R^2$, $R^3$ and $R^4$=H) and glycerol carbonate ($R^1$=$CH_2OH$ and $R^2$, $R^3$ and $R^4$=H). Propylene carbonate is very particularly preferably suitable.

Ethylene carbonate is a colorless crystalline compound which melts at 39° C. and boils at 238° C. Ethylene carbonate, which is readily soluble in water, alcohols and organic solvents, may be manufactured by large-scale industrial synthesis methods from ethylene oxide and liquid $CO_2$. Propylene carbonate is a water-clear, highly mobile liquid, with a density of 1.2057 gcm$^{-3}$; its melting point is at −49° C. and its boiling point at 242° C. Propylene carbonate is also obtainable on a large industrial scale by reacting propylene oxide and $CO_2$ at 200° C. and 80 bar. Glycerol carbonate is obtainable by transesterifying ethylene carbonate or dimethyl carbonate with glycerol, with ethylene glycol or methanol being obtained as secondary products. Another synthetic pathway starts from glycidol (2,3-epoxy-1-propanol), which is reacted under pressure in the presence of catalysts with $CO_2$ to yield glycerol carbonate. Glycerol carbonate is a clear, highly mobile liquid with a density of 1.398 gcm$^{-3}$, which boils at 125-130° C. (0.15 mbar).

Preferred compounds of formula H—(O—$CH_2CH_2$)$_n$—OR with R=hydrogen atom, methyl group and n=1, 2, 3 or 4 are chosen from ethylene glycol, diethylene glycol, diethylene glycol monomethyl ether.

It is particularly preferred to use a mixture of
ethylene glycol and isopropanol,
or of
isopropanol, propylene carbonate and diethylene glycol
as the organic solvent.

Organic solvents are used in agent A3 preferably in a quantity of 0.5 to 20 wt. %, particularly 2 to 10 wt. %, very particularly 3 to 6 wt. %, based on weight of agent A3.

For a particularly preferred embodiment, the dyeing agent is present in the kit as the following components:
agent A1 contains in a liquid cosmetic carrier at least one CH-acidic compound and exhibits a pH value of 0.5 to 2.5 and agent A2 contains in a liquid cosmetic carrier at least one reactive carbonyl compound and exhibits a pH value of 2 to 5.

Formulations which are particularly stable in storage may be obtained if agent A1 exhibits a pH value of 1 to 2 and particularly preferably a pH value of 1.1 to 1.9; this pH range is thus preferred.

It is furthermore preferred for agent A2 to exhibit a pH value of 3 to 5, particularly 3.2 to 4.5.

The pH values for the purposes of the present invention are pH values which were measured at a temperature of 22° C.

The pH value of agents A1 and/or A2 may be adjusted with the assistance of an organic or inorganic acid such as hydrochloric acid, sulfuric acid, hydrobromic acid, phosphoric acid, acetic acid, tartaric acid, citric acid, lactic acid, malic acid or glycolic acid.

It is particularly preferred in this connection to adjust the pH values with the assistance of hydrochloric acid, tartaric acid, citric acid, malic acid or lactic acid.

The kit according to the invention may be used by intimately mixing agents A1 and A2 with one another shortly before application onto the hair fibers. In order to further improve the dyeing result, it may be advantageous to carry out the dyeing in an alkaline pH range.

For a particular embodiment, the kit may additionally include a third, previously described liquid cosmetic agent A3 (see above) having at least one alkalizing agent in a cosmetic carrier and exhibiting a pH value of greater than 7. This embodiment of the kit is equally preferred for all embodiments of agents A1 and A2 (i.e., both for the embodiment of A1 and A2 as a solid (powder, granules or moldings) and for the embodiment of A1 and A2 as liquids with a specific pH value).

According to the invention, preferred kits are those wherein agents A1, A2 and A3 are such that the ready-to-use dyeing agent exhibits a pH value of greater than 7.

Liquid cosmetic agents A3 preferably additionally contain at least one alkalizing agent.

Alkalizing agents in liquid cosmetic agent A3 are preferably chosen from at least one alkalizing agent from ammonia, basic amino acids, alkali metal hydroxides, alkanolamines, alkali metal metasilicates, urea, morpholine, N-methylglucamine, imidazole, alkali metal phosphates and alkali metal hydrogenphosphates. Preferably used alkali metal ions are lithium, sodium, potassium, particularly sodium or potassium.

Basic amino acids usable as an alkalizing agent according to the invention are preferably chosen from L-arginine, D-arginine, D,L-arginine, L-histidine, D-histidine, D,L-histidine, L-lysine, D-lysine, D,L-lysine, particularly preferably L-arginine, D-arginine, D,L-arginine.

Alkali metal hydroxides usable as an alkalizing agent according to the invention are preferably chosen from sodium hydroxide and potassium hydroxide.

Alkanolamines usable as an alkalizing agent according to the invention are preferably chosen from primary amines with a $C_2$-$C_6$ alkyl parent substance bearing at least one hydroxyl group. Particularly preferred alkanolamines are chosen from 2-aminoethan-1-ol(monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Alkanolamines which are very particularly preferred according to the invention are chosen from 2-aminoethan-1-ol, 2-amino-2-methylpropan-1-ol and 2-amino-2-methylpropane-1,3-diol.

The alkalizing agent is particularly preferably chosen from ammonia, 2-aminoethanol, 2-amino-2-methylpropan-1-ol, 2-amino-2-methylpropane-1,3-diol, potassium hydroxide, sodium hydroxide, L-arginine, D-arginine, DL-arginine, N-methylglucamine, morpholine, imidazole, urea and mixtures thereof.

Buffer systems adjusted to a pH value of greater than 7 may furthermore also be used in the liquid cosmetic agent A3.

According to the invention, a pH buffer system is considered to be those chemical compounds or a combination of chemical compounds which, in a solution, ensure that the pH value of the solution changes only slightly on addition of a small quantity of acid or alkali solution to a volume of the cosmetic carrier. This change is less pronounced than is the case on addition of the same quantity of acid or alkali solution to an identical volume of the cosmetic carrier without the pH buffer system.

Such pH buffer systems are preferably chosen from at least one representative from hydrogencarbonate/carbonate, edible acid (particularly citric acid)/monohydrogenphosphate, edible acid (particularly citric acid)/dihydrogenphosphate, tris(hydroxymethyl)aminomethane/maleic acid/NaOH, tris(hydroxymethyl)aminomethane/maleic acid/KOH, tris(hydroxymethyl)aminomethane/HCl, monohydrogenphosphate/dihydrogenphosphate, dihydrogenphosphate/NaOH, dihydrogenphosphate/KOH, $H_3BO_3$/KCl/NaOH, $H_3BO_3$/KCl/KOH, borate/HCl, borate/halide (particularly chloride, such as potassium chloride)/NaOH, borate/halide (particularly chloride such as potassium chloride)/KOH, Teorell-Stenhagen buffer system, McIlvaine buffer system, glycine/NaOH and glycine/KOH. Particularly preferred pH buffer systems are chosen from at least one representative from tris(hydroxymethyl)aminomethane/maleic acid/NaOH, tris(hydroxymethyl)aminomethane/maleic acid/KOH, tris(hydroxymethyl)aminomethane/HCl, borate/HCl, and $H_3BO_3$/KCl/NaOH.

The pH buffer systems indicated with a slash in the above list are mixtures of the compounds separated by the slash. Anionic compounds mentioned in the list are used in the form of their salts with a corresponding mono- or polyvalent cation. Preferred cations are alkali metal cations (in particular sodium or potassium) and ammonium ions. Edible acids usable according to the invention in the buffer systems include citric acid, tartaric acid, malic acid or mixtures thereof.

The pH-buffer system is preferably present in the ready-to-use dyeing agent in a quantity of 0.1 to 10.0 wt. %, more preferably 0.3 to 5.0 wt. %, even more preferably 0.5 to 3.0 wt. %, each based on weight of the application mixture prepared from agent A1 and agent A2 or from agents A1, A2 and A3.

The pH value of the ready-to-use dyeing agent produced by mixing agents A1, A2 and A3 is preferably from 7.5 to 11. It is preferred for the pH value of the ready-to-use dyeing agent to be in a range from 8 to 10.

In a further embodiment of the kit, the ready-to-use dyeing agent or agent A1 and/or agent A2 may additionally contain at least one developer component and optionally at least one coupler component as oxidation dye precursors. It is however preferred to formulate the agents according to the invention without oxidation dye precursors, in particular if it is intended to minimize the risk of allergy. A preferred kit according to the invention is thus characterized in that the ready-to-use dyeing agent or the agents A1 and A2 contain(s) no oxidation dye precursors, in particular of the developer type.

The ready-to-use dyeing agent, or agents A1 and/or A2, may furthermore additionally contain at least one direct dye.

These are dyes which key directly to the hair and do not need an oxidative process to develop the color. Direct dyes are conventionally nitrophenylenediamines, nitroaminophenols, azo dyes, anthraquinones or indophenols.

The direct dyes are used preferably in a quantity of 0.001 to 20 wt. %, relative to the entire application preparation. The total quantity of direct dyes preferably amounts to at most 20 wt. %.

Direct dyes may be subdivided into anionic, cationic and nonionic direct dyes.

Preferred anionic direct dyes are the compounds known by the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred nonionic direct dyes are the compounds known by the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2'-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenol)amino]-benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol.

Furthermore, naturally occurring dyes such as are contained for example in henna red, henna neutral, henna black, chamomile flowers, sandalwood, black tea, alder buckthorn bark, sage, logwood, madder root, catechu, lotus tree and alkanet root may also be used as direct dyes.

Agents according to the invention may contain the optionally present direct dyes in a quantity of 0.01 to 20.00 wt. %, relative to the kit according to the invention and thus relative to the ready-to-use dyeing agent. Furthermore, the kit may also contain naturally occurring dyes such as are present in henna red, henna neutral, henna black, chamomile flowers, sandalwood, black tea, alder buckthorn bark, sage, logwood, madder root, catechu, lotus tree and alkanet root.

Decolorizing agent B of the kit contains hydrogen peroxide in a cosmetic carrier.

Preferred decolorizing agents B contain hydrogen peroxide in quantities of from 0.5 to 12 wt. %, preferably 1 to 6 wt. %, more preferably 1 to 4 wt. %, and even more preferably 1.5 to 3 wt. %, based on weight of the entire agent.

Decolorizing agent B preferably has a pH value of 4 to 11, more preferably 5 to 10, and even more preferably 7 to 10.

It is further preferred for the decolorizing agent B to contain, in addition to hydrogen peroxide, less than 0.001 wt. % of further peroxo compounds. For the purposes of the invention it contains no further peroxo compounds. Peroxo compounds are chemical compounds which contain the —O—O— or $O_2^{2-}$ group in their molecule.

Hydrogen peroxide and perhydrates do not fall within the definition of peroxo compounds for the purposes of this embodiment of decolorizing agent B.

Peroxo compounds which are preferably avoided are organic peracids, peroxydisulfate salts, persulfate salts, peroxydiphosphate salts (in particular ammonium peroxydisulfate, potassium peroxydisulfate, sodium peroxydisulfate, ammonium persulfate, potassium persulfate, sodium persulfate, potassium peroxydiphosphate) and peroxides (such as barium peroxide and magnesium peroxide). Preferred decolorizing agents are thus those which do not contain organic peracids and peroxydisulfate salts and persulfate salts and peroxydiphosphate salts and peroxides.

It is preferred according to the invention for the decolorizing agent B additionally to contain at least one surfactant. In many cases, the ready-to-use dyeing agents contain at least one surfactant, with in principle not only anionic but also zwitterionic, ampholytic, nonionic and cationic surfactants being suitable. In many cases, however, it has proven advantageous to select the surfactants from among anionic, zwitterionic or nonionic surfactants.

Anionic surfactants which are suitable in the agents (in particular, A1, A2, A3, B) are any anionic surface-active substances suitable for use on the human body. These have an anionic water-solubilizing group such as a carboxylate, sulfate, sulfonate or phosphate group and a lipophilic alkyl group having approximately 10 to 22 C atoms. The molecule may additionally contain glycol or polyglycol ether groups, ester, ether and amide groups and hydroxyl groups. Examples of suitable anionic surfactants are, each in the form of sodium, potassium and ammonium and mono-, di- and trialkanolammonium salts having 2 or 3 C atoms in the alkanol group, linear fatty acids having 10 to 22 C atoms (soaps),
ether carboxylic acids of formula R—O—(CH$_2$—CH$_2$O)$_x$—CH$_2$—COOH, wherein R is a linear alkyl group having 10 to 22 C atoms and x=0 or 1 to 16,
acyl sarcosides having 10 to 18 C atoms in the acyl group,
acyl taurides having 10 to 18 C atoms in the acyl group,
acyl isethionates having 10 to 18 C atoms in the acyl group,
sulfosuccinic acid mono- and dialkyl esters having 8 to 18 C atoms in the alkyl group and sulfosuccinic acid monoalkyl polyoxyethyl esters having 8 to 18 C atoms in the alkyl group and 1 to 6 oxyethyl groups,
linear alkane sulfonates having 12 to 18 C atoms,
linear alpha-olefin sulfonates having 12 to 18 C atoms,
alpha-sulfofatty acid methyl esters of fatty acids having 12 to 18 C atoms,
alkyl sulfates and alkyl polyglycol ether sulfates of formula R—O(CH$_2$—CH$_2$O)$_x$—SO$_3$H, in which R is a preferably linear alkyl group having 10 to 18 C atoms and x=0 or 1 to 12,
anionic alkyl oligoglycosides or anionic alkenyl oligoglycoside derivatives, selected from alkyl and/or alkenyl oligoglycoside carboxylates, sulfates, phosphates and/or isethionates derived from alkyl and/or alkenyl oligoglycosides of the general formula (II),

R—O-(G)$_p$     (II)

with the meaning
R C$_{6-22}$ alkyl or C$_{6-22}$ alkenyl,
G glycoside unit which is derived from a sugar having 5 or 6 carbon atoms,
p number from 1 to 10,
in particular lauryl glucoside carboxylate, as may be obtained as Plantapon® LGC from Cognis Deutschland,
mixtures of surface-active hydroxysulfonates according to DE-A-37 25 030,
sulfated hydroxyalkyl polyethylene and/or hydroxyalkylene propylene glycol ethers according to DE-A-37 23 354,
sulfonates of unsaturated fatty acids having 12 to 24 C atoms and 1 to 6 double bonds according to DE-A-39 26 344, esters of tartaric acid and citric acid with alcohols, which are addition products of approx. 2-15 molecules of ethylene oxide and/or propylene oxide onto fatty alcohols having 8 to 22 C atoms.

Preferred anionic surfactants are alkyl sulfates, alkyl polyglycol ether sulfates and ether carboxylic acids having 10 to 18 C atoms in the alkyl group and up to 12 glycol ether groups per molecule and in particular salts of saturated and in particular unsaturated $C_8$-$C_{22}$ carboxylic acids, such as oleic acid, stearic acid, isostearic acid and palmitic acid.

Nonionic surfactants contain as hydrophilic group for example a polyol group, a polyalkylene glycol ether group or a combination of a polyol group and polyglycol ether group. Such compounds include addition products of 2 to 60 mol of ethylene oxide and/or 0 to 5 mol of propylene oxide onto linear fatty alcohols having 8 to 22 C atoms, onto fatty acids having 12 to 22 C atoms and onto alkylphenols having 8 to 15 C atoms in the alkyl group, $C_{12}$-$C_{22}$ fatty acid mono- and diesters of addition products of 1 to 30 mol of ethylene oxide onto glycerol, $C_8$-$C_{22}$ alkyl mono- and oligoglycosides and the ethoxylated analogues thereof, and addition products of 5 to 60 mol of ethylene oxide onto castor oil and hardened castor oil.

Preferred nonionic surfactants are alkyl polyglycosides of the general formula $R^1O$—$(Z)_x$. These compounds are characterized by the following parameters.

The alkyl residue $R^1$ contains 6 to 22 carbon atoms and may be both linear and branched. Primary linear aliphatic residues and those methyl-branched in position 2 are preferred. Such alkyl residues are for example 1-octyl, 1-decyl, 1-lauryl, 1-myristyl, 1-cetyl and 1-stearyl. 1-Octyl, 1-decyl, 1-lauryl, 1-myristyl are particularly preferred. When "oxo alcohols" are used as starting materials, compounds having an uneven number of carbon atoms in the alkyl chain predominate.

Alkyl polyglycosides usable according to the invention may contain only one specific alkyl residue $R^1$. Conventionally, however, these compounds are produced starting from natural fats and oils or mineral oils. In this case, alkyl residues R which are present are mixtures corresponding to the starting compounds or corresponding to the particular processing of these compounds.

Particularly preferred such alkyl polyglycosides are those in which $R^1$ substantially consists of $C_8$ and $C_{10}$ alkyl groups,
substantially consists of $C_{12}$ and $C_{14}$ alkyl groups,
substantially consists of $C_8$ to $C_{16}$ alkyl groups. or
substantially consists of $C_{12}$ to $C_{16}$ alkyl groups.

Any desired mono- or oligosaccharides may be used as the sugar building block Z. Sugars having 5 or 6 carbon atoms and the corresponding oligosaccharides are conventionally used. Such sugars are for example glucose, fructose, galactose, arabinose, ribose, xylose, lyxose, allose, altrose, mannose, gulose, idose, talose and sucrose. Preferred sugar building blocks are glucose, fructose, galactose, arabinose and sucrose; glucose is particularly preferred.

Alkyl polyglycosides usable according to the invention contain on average 1.1 to 5 sugar units. Alkyl polyglycosides with x values of 1.1 to 1.6 are preferred. Alkyl glycosides in which x is 1.1 to 1.4 are very particularly preferred.

In addition to their surfactant action, the alkyl glycosides may also serve to improve the fixing of scent components to the hair. In the event that an action of the perfume oil on the hair extending beyond the duration of the hair treatment is desired, a person skilled in the art will preferably make use of this class of substances as a further ingredient of the preparations according to the invention.

The alkoxylated homologues of the stated alkyl polyglycosides may also be used according to the invention. These homologues may contain on average up to 10 ethylene oxide and/or propylene oxide units per alkyl glycoside unit.

Examples of such nonionic surfactants are distributed under the trade name Cremophor® RH40 (hydrogenated castor oil with approx. 40-45 EO units (INCI name: PEG-40 Hydrogenated Castor Oil)) by BASF or Mergital® CS 50A (fatty alcohol with approx. 50 EO units (INCI name: Ceteareth-50)) by Cognis.

Zwitterionic surfactants may furthermore be used, particularly as co-surfactants. Those surface-active compounds having at least one quaternary ammonium group and at least one —$COO^{(-)}$ or —$SO_3^{(-)}$ group on each molecule are designated as zwitterionic surfactants. Particularly suitable zwitterionic surfactants are "betaines" such as N-alkyl-N,N-dimethylammonium glycinates, for example cocoalkyldimethylammonium glycinate, N-acylaminopropyl-N,N-dimethylammonium glycinates, for example cocoacylaminopropyl-dimethylammonium glycinate, and 2-alkyl-3-carboxymethyl-3-hydroxyethylimidazolines having in each case 8 to 18 C atoms in the alkyl or acyl group and cocoacylaminoethylhydroxyethyl-carboxymethyl glycinate. One preferred zwitterionic surfactant is the fatty acid amide derivative known by the INCI name Cocamidopropyl Betaine.

Ampholytic surfactants are likewise suitable as co-surfactants Ampholytic surfactants refer to those surface-active compounds which, in addition to a $C_8$-$C_{18}$ alkyl or acyl group, have at least one free amino group and at least one —COOH or —$SO_3H$ group per molecule and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case approx. 8 to 18 C atoms in the alkyl group. Particularly preferred ampholytic surfactants are N-cocoalkyl aminopropionate, cocoacylaminoethyl aminopropionate and $C_{12-18}$-acyl sarcosine.

Useful cationic surfactants according to the invention include those of the quaternary ammonium compound, ester quat and amidoamine type.

Preferred quaternary ammonium compounds are ammonium halides, in particular chlorides and bromides, such as alkyltrimethylammonium chlorides, dialkyldimethylammonium chlorides and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, and the imidazolinium compounds known under the INCI names Quaternium-27 and Quaternium-83. The long alkyl chains of the above-stated surfactants preferably comprise 10 to 18 carbon atoms.

Ester quats are known substances which contain both at least one ester function and at least one quaternary ammonium group as a structural element. Preferred ester quats are quaternized ester salts of fatty acids with triethanolamine, quaternized ester salts of fatty acids with diethanolalkylamines and quaternized ester salts of fatty acids with 1,2-dihydroxypropyl-dialkylamines. Such products are distributed, for example, under the trademarks Stepantex®, Dehyquart® and Armocare®. The products Armocare® VGH-70, an N,N-bis(2-palmitoyloxyethyl)dimethylammonium chloride, and Dehyquart® F-75 and Dehyquart® AU-35 are examples of such ester quats.

The alkylamidoamines are conventionally produced by amidating natural or synthetic fatty acids and fatty acid cuts with dialkylaminoamines. One compound from this group of substances which is particularly suitable according to the invention is stearamidopropyldimethylamine which is commercially available under the name Tegoamid® S 18.

Quaternized protein hydrolysates are further cationic surfactants which are usable according to the invention.

Cationic silicone oils are likewise suitable according to the invention, such as for example the commercially obtainable products Q2-7224 (manufacturer: Dow Corning; a stabilized trimethylsilylamodimethicone), Dow Corning 929 Emulsion (containing a hydroxylamino-modified silicone which is also designated an amodimethicone), SM-2059 (manufacturer: General Electric), SLM-55067 (manufacturer: Wacker) and Abil®-Quat 3270 and 3272 (manufacturer: Th. Goldschmidt; diquaternary polydimethylsiloxane, Quaternium-80).

One example of a quaternary sugar derivative usable as a cationic surfactant is the commercial product Glucquat®100, according to INCI nomenclature a "Lauryl Methyl Gluceth-10 Hydroxypropyl Dimonium Chloride".

Compounds with alkyl groups used as surfactant may comprise uniform substances. It is, however, generally preferred to start from native plant or animal raw materials when producing these substances, such that mixtures of substances having differing alkyl chain lengths depending on the particular raw material are obtained.

Surfactants which are addition products of ethylene and/or propylene oxide onto fatty alcohols or derivatives of these addition products may be used both as products with a "normal" homolog distribution and as products with a narrow homolog distribution. A "normal" homolog distribution is here taken to mean mixtures of homologs which are obtained on reacting fatty alcohol and alkylene oxide using alkali metals, alkali metal hydroxides or alkali metal alkoxides as catalysts. Narrow homolog distributions, in contrast, are obtained if hydrotalcite, alkaline earth metal salts of ether carboxylic acids, alkaline earth metal oxides, hydroxides or alkoxides are for example used as catalysts. It may be preferred to use products with a narrow homolog distribution.

Agents A1, A2 and A3 may additionally contain at least one surfactant.

Agents A1, A2, A3 and/or the decolorizing agent B of the kit according to the invention may additionally contain at least one silicone. Silicones, if present in the stated agents, are preferably contained in quantities of 0.05 to 5 wt. %, preferably of 0.2 to 5 wt. %, each based on weight of the ready-to-use agent.

Silicones are particularly preferably selected from among at least one representative of the list made up of:
i) polyalkylsiloxanes, polyarylsiloxanes, polyalkylarylsiloxanes, which are volatile or non-volatile, straight-chain, branched or cyclic, crosslinked or uncrosslinked;
ii) polysiloxanes which contain in their general structure one or more organofunctional groups selected from:
   a) substituted or unsubstituted aminated groups;
   b) (per)fluorinated groups;
   c) thiol groups;
   d) carboxylate groups;
   e) hydroxylated groups;
   f) alkoxylated groups;
   g) acyloxyalkyl groups;
   h) amphoteric groups;
   i) bisulfite groups;
   j) hydroxyacylamino groups;
   k) carboxy groups;
   l) sulfonic acid groups; and
   m) sulfate or thiosulfate groups;
iii) linear polysiloxane(A)/polyoxyalkylene(B) block copolymers of the type $(A-B)_n$ with n >3;
iv) grafted silicone polymers having an organic parent structure containing no silicone, which polymers consist of an organic main chain which is formed from organic monomers containing no silicone and onto which at least one polysiloxane macromer has been grafted in the chain and optionally onto at least one chain end;
v) grafted silicone polymers having a polysiloxane parent structure onto which organic monomers containing no silicone have been grafted, which polymers comprise a polysiloxane main chain onto which at least one organic macromer containing no silicone has been grafted in the chain and optionally onto at least one of the ends thereof, such as for example the commercial product Abil B 8832 from Degussa which is distributed under INCI name Bis-PEG/PPG-20/20 Dimethicone;
vi) or mixtures thereof.

Agents A1, A2, A3 and/or decolorizing agent B may additionally contain at least one protein hydrolysate. Protein hydrolysates are product mixtures which are obtained by acidically, basically or enzymatically catalysed degradation of proteins.

Protein hydrolysates of both plant and animal origin may be used according to the invention.

Animal protein hydrolysates include elastin, collagen, keratin, silk and milk protein hydrolysates, which may also assume salt form. Such products are distributed, for example, under the trademarks Keratin DEC® (Vincience), Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda). Preferably, protein hydrolysates of plant origin such as soy, almond, rice, pea, potato and wheat protein hydrolysates are used. Such products are obtainable, for example, under the trademarks Gluadin® (Cognis), DiaMin® (Diamalt), Lexein® (Inolex) and Crotein® (Croda).

Although the use of protein hydrolysates is preferred per se, amino acid mixtures or individual amino acids such as for example arginine, lysine, histidine or pyroglutamic acid obtained in a different manner may optionally also be used instead. It is likewise possible to use derivatives of protein hydrolysates, for example in the form of the fatty acid condensation products thereof Such products are distributed, for example, under the names Lamepon® (Cognis), Gluadin® (Cognis), Lexein® (Inolex), Crolastin® (Croda) or Crotein® (Croda).

Protein hydrolysates are preferably present in a quantity of 0.05 to 5 wt. %, particularly preferably of 0.5 to 2.0 wt. %, relative to the weight of the ready-to-use dying agent or of the decolorizing agent B.

In a further embodiment of the kit, the agents A1, A2, A3 and/or the decolorizing agent B may additionally contain at least one cationic and/or at least one amphoteric polymer.

Cationic polymers are polymers which comprise groups in the main and/or side chain which may be "temporarily" or "permanently" cationic. Polymers which are designated "permanently cationic" according to the invention are those which, irrespective of the pH value of the agents, comprise a cationic group. As a rule, these are polymers which contain a quaternary nitrogen atom, for example in the form of an ammonium group. Preferred cationic groups are quaternary ammonium groups. Polymers which have proven particularly suitable are in particular those in which the quaternary ammonium group is bound via a $C_{1-4}$ hydrocarbon group to a main polymer chain synthesized from acrylic acid, methacrylic acid or the derivatives thereof Homopolymers of the general formula (P1),

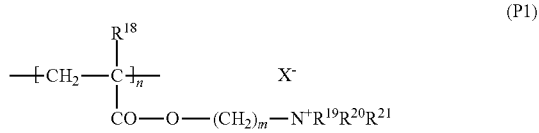

$R^{18}$ is —H or —$CH_3$, $R^{19}$, $R^{20}$ and $R^{21}$ are mutually independently chosen from $C_{1-4}$ alkyl, alkenyl or hydroxyalkyl groups; m=1, 2, 3 or 4; n is a natural number; and $X^-$ a physiologically acceptable organic or inorganic anion, and copolymers substantially consisting of the monomer units listed in formula (P1) and nonionogenic monomer units are particularly preferred cationic polymers. In the context of these polymers, those which are preferred according to the invention are those for which at least one of the following conditions applies:

$R^{18}$ of formula (P1) is a methyl group,
$R^{19}$, $R^{20}$ and $R^{21}$ of formula (P1) are methyl groups, and
m of formula (P1) has the value 2.

Physiologically acceptable counterions $X^-$ of formula (P1) which may be considered are halide ions, sulfate ions, phosphate ions, methosulfate ions and organic ions such as lactate, citrate, tartrate and acetate ions. Halide ions, in particular chloride, are preferred.

One particularly suitable homopolymer is poly(methacryloyloxyethyltrimethylammonium chloride) with the INCI name Polyquaternium-37, which can be crosslinked. The homopolymer is preferably used in the form of a nonaqueous polymer dispersion which should comprise a polymer fraction of no less than 30 wt. %. Such polymer dispersions are commercially available under the names Salcare® SC 95 (approx. 50% polymer fraction, further components: mineral oil (INCI name: Mineral Oil) and tridecyl-polyoxypropylene-polyoxyethylene ether (INCI name: PPG-1-Trideceth-6)) and Salcare® SC 96 (approx. 50% polymer fraction, further components: mixture of diesters of propylene glycol with a mixture of caprylic and capric acid (INCI name: Propylene Glycol Dicaprylate/Dicaprate) and tridecyl-polyoxypropylene-polyoxyethylene ether (INCI name: PPG-1-Trideceth-6)).

Copolymers with monomer units of formula (III) preferably contain acrylamide, methacrylamide, acrylic acid $C_{1-4}$ alkyl esters and methacrylic acid $C_{1-4}$ alkyl esters as nonionogenic monomer units. Acrylamide is particularly preferred among these nonionogenic monomers. These copolymers, as described above for the homopolymers, may also be crosslinked. A copolymer which is preferred according to the invention is crosslinked acrylamide-methacryloyloxyethyltrimethylammonium chloride copolymer. Such copolymers, in which the monomers are present in a weight ratio of approx. 20:80, are commercially available as approx. 50% nonaqueous polymer dispersions under the name Salcare® SC 92.

Further preferred cationic polymers include—
quaternized cellulose derivatives, as are commercially available under the names Celquat® and Polymer JR®. The compounds Celquat® H 100, Celquat® L 200 and polymer JR®400 are preferred quaternized cellulose derivatives,
cationized honey, for example, the commercial product Honeyquat® 50,
cationic guar derivatives, such as in particular the products distributed under the trade names Cosmedia®Guar and Jaguar®,
polysiloxanes with quaternary groups, such as the commercially obtainable products Q2-7224 (manufacturer: Dow Corning; a stabilized trimethylsilylamodimethicone), Dow Corning® 929 Emulsion (containing a hydroxylamino-modified silicone which is also designated an amodimethicone), SM-2059 (manufacturer: General Electric), SLM-55067 (manufacturer: Wacker) and Abil®-Quat 3270 and 3272 (manufacturer: Th. Goldschmidt; diquaternary polydimethylsiloxane, Quaternium-80).
polymeric dimethyldiallylammonium salts and the copolymers thereof with esters and amides of acrylic acid and methacrylic acid. The products commercially available under the names Merquat®100 (poly(dimethyldiallylammonium chloride)) and Merquat®550 (dimethyldiallylammonium chloride-acrylamide copolymer) are examples of such cationic polymers,
copolymers of vinylpyrrolidone with quaternized derivatives of dialkylaminoalkyl acrylate and methacrylate, such as for example vinylpyrrolidone-dimethylaminoethyl methacrylate copolymers quaternized with diethyl sulfate. Such compounds are commercially available under the names Gafquat®734 and Gafquat®755,
vinylpyrrolidone-vinylimidazolium methochloride copolymers, as are offered for sale under the names Luviquat® FC 370, FC 550, FC 905 and HM 552,
quaternized polyvinyl alcohol,
and the polymers with quaternary nitrogen atoms in the polymer main chain known under the names
Polyquaternium 2 (for example, Mirapol® A-15 from Rhodia),
Polyquaternium 17,
Polyquaternium 18, and
Polyquaternium 27.

Polymers known under the names Polyquaternium-24 (commercial product, for example Quatrisoft® LM 200) may also be used as cationic polymers. Copolymers of vinylpyrrolidone, as are available as commercial products Copolymer 845 (manufacturer: ISP), Gaffix® VC 713 (manufacturer: ISP), Gafquat®ASCP 1011, Gafquat®HS 110, Luviquat®8155 and Luviquat® MS 370 may likewise be used according to the invention.

Further cationic polymers according to the invention are "temporarily cationic" polymers. These polymers conventionally contain an amino group which at specific pH values assumes the form of a quaternary ammonium group and is thus cationic. Chitosan and the derivatives thereof are for example preferred, as are readily commercially available for example under the trade names Hydagen® CMF, Hydagen® HCMF, Kytamer® PC and Chitolam® NB/101. Chitosans are deacetylated chitins which are commercially available in various degrees of deacetylation and various degrees of degradation (molecular weights). The production thereof is described, for example, in DE 44 40 625 A1 and in DE 1 95 03 465 A1.

Particularly highly suitable chitosans exhibit a degree of deacetylation of at least 80% and a molecular weight of $5 \cdot 10^5$ to $5 \cdot 10^6$ (g/mol).

In order to produce preparations according to the invention, the chitosan must be converted into the salt form. This may proceed by dissolution in dilute aqueous acids. Suitable acids are both mineral acids such as for example hydrochloric acid, sulfuric acid and phosphoric acid and organic acids, for example low molecular weight carboxylic acids, polycarboxylic acids and hydroxycarboxylic acids. Relatively high molecular weight alkylsulfonic acids or alkylsulfuric acids or organophosphoric acids may furthermore be used, provided that they have the necessary physiological acceptability. Suitable acids for converting the chitosans into the salt form are for example acetic acid, glycolic acid, tartaric acid, malic acid, citric acid, lactic acid, 2-pyrrolidinone-5-carboxylic acid, benzoic acid or salicylic acid. Low molecular weight hydroxycarboxylic acids such as for example glycolic acid or lactic acid are preferably used.

Amphoteric polymers refer to those polymers
  having both free amino groups and free —COOH— or $SO_3H$ groups in each molecule and are capable of forming internal salts,
  zwitterionic polymers having quaternary ammonium groups and —COO⁻ groups or —$SO_3^-$ groups in each molecule, and
  polymers having —COOH groups or $SO_3H$ groups and quaternary ammonium groups.

Polymers with quaternary ammonium groups stated in the list are preferably used according to the invention as amphoteric polymers.

One example of an amphoteric polymer usable according to the invention is the acrylic resin obtainable under the name Amphomer®, which is a copolymer of tert.-butylaminoethyl methacrylate, N-(1,1,3,3-tetramethylbutyl)acrylamide and two or more monomers from the group acrylic acid, methacrylic acid and the simple esters thereof.

Further amphoteric polymers usable according to the invention are the compounds stated in British published patent application 2 104 091, European published patent application 47 714, European published patent application 217 274, European published patent application 283 817 and German published patent application 28 17 369.

The amphoteric polymers may generally be used according to the invention both directly and in salt form, which is obtained by neutralization of the polymers, for example with an alkali metal hydroxide.

Further active ingredients and auxiliary substances and additives include—
  nonionic polymers such as vinylpyrrolidone/vinyl acrylate copolymers, polyvinylpyrrolidone and vinylpyrrolidone/vinyl acetate copolymers and polysiloxanes,
  anionic polymers such as polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.-butylacrylamide terpolymers,
  thickeners such as agar-agar, guar gum, alginates, xanthan gum, gum arabic, karaya gum, locust bean flour, linseed gums, dextrans, cellulose derivatives, for example methylcellulose, hydroxyalkylcellulose and carboxymethylcellulose, starch fractions and derivatives such as amylose, amylopectin and dextrins, clays such as bentonite or completely synthetic hydrocolloids such as for example polyvinyl alcohol,
  structuring agents such as glucose and maleic acid,
  perfume oils, dimethyl isosorbide and cyclodextrins,
  antidandruff active ingredients such as piroctone olamine and zinc omadine,
  active ingredients such as panthenol, pantothenic acid, allantoin, pyrrolidonecarboxylic acids and the salts thereof, plant extracts and vitamins,
  cholesterol,
  light stabilizers,
  consistency providers such as sugar esters, polyol esters or polyol alkyl ethers,
  fats and waxes such as spermaceti, beeswax, montan wax, paraffins, fatty alcohols and fatty acid esters,
  fatty acid alkanolamides,
  complexing agents such as EDTA, NTA and phosphonic acids,
  swelling and penetrating substances such as glycerol, propylene glycol monoethyl ether, carbonates, hydrogencarbonates, guanidines, ureas and primary, secondary and tertiary phosphates, imidazoles, tannins, pyrrole,
  opacifiers such as latex,
  pearlescent agents such as ethylene glycol mono- and distearate,
  propellants such as propane/butane mixtures, $N_2O$, dimethyl ether, $CO_2$ and air, together with
  antioxidants.

Components of the cosmetic carrier are used to produce the agents A1, A2, A3 or the decolorizing agent B in quantities conventional for this purpose; for example, emulsifiers are used in concentrations of 0.5 to 30 wt. % and thickeners in concentrations of 0.1 to 25 wt. % relative to the particular agent.

The present invention secondly provides a method for decolorizing dyed keratin-containing fibers, in particular human hair, characterized in that a decolorizing agent containing hydrogen peroxide in a cosmetic carrier is applied onto the keratin-containing fibers dyed with a dyeing agent containing a combination of at least one CH-acidic compound with at least one reactive carbonyl compound in a cosmetic carrier, is left on the fibers for 1 to 30 minutes and then rinsed back out.

It is here preferred to use decolorizing agents B which are preferred according to the first subject matter of the invention as the decolorizing agent. All preferred embodiments of the decolorizing agent B of the first subject matter of the invention here apply mutatis mutandis.

Furthermore, keratin-containing fibers to be decolorized have preferably been dyed using the preferred ready-to-use dyeing agent described for the purposes of the first subject matter of the invention. The preferred embodiments thus apply here too mutatis mutandis.

It is preferred according to the invention to leave the decolorizing agent on the fibers for 5 to 20 minutes.

The present invention thirdly provides the use of a composition containing hydrogen peroxide in a cosmetic carrier for gently decolorizing dyed keratin-containing fibers which have been dyed with a dyeing agent containing a combination of at least one CH-acidic compound with at least one reactive carbonyl compound in a cosmetic carrier.

It is here preferred to use decolorizing agents B which are preferred according to the first subject matter of the invention as the compositions. All preferred embodiments of the decolorizing agent B of the first subject matter of the invention here apply mutatis mutandis.

Furthermore, the dyed keratin-containing fibers to be decolorized have preferably been dyed using the preferred ready-to-use dyeing agent described for the purposes of the first subject matter of the invention. The preferred embodiments thus apply here mutatis mutandis.

EXAMPLES

Unless otherwise stated, the quantities stated in the examples are weight percentages.

1.0 Provision of Agents A1—

The following agents A1 were provided according to Table 1:

TABLE 1

| Component | A1a | A1b | A1c |
|---|---|---|---|
| 1,2-Dihydro-1,3,4,6-tetramethyl-2-oxo- | 10 mmol | — | — |
| 1-Allyl-1,2-dihydro-3,4,6-trimethyl-2-oxopyrimidinium bromide | — | 10 mmol | — |
| 2-(Cyanomethyl)benzimidazole | — | — | 10 mmol |
| N-Hance ® 3196 | — | — | 1.2 |
| Carbopol ETD 2020 ® | 1.0 | — | — |
| Xanthan gum | — | 1.6 | — |
| Sodium benzoate | 0.3 | — | 0.6 |
| Propylparaben | 0.15 | 0.5 | — |
| Potassium chloride | 0.37 | — | — |
| 0.2 mol/L HCl solution | 0.07 | — | — |
| Tartaric acid | Ad pH | Ad pH | Ad pH |
| Water | Ad 100 | Ad 100 | Ad 100 |

1-Allyl-1,2-dihydro-3,4,6-trimethyl-2-oxopyrimidinium bromide and/or 2-(cyanomethyl)benzimidazole were dissolved with stirring in 70 g of water at a temperature of 80 to 90° C. and then the proportions of the components sodium benzoate, potassium chloride, 0.2 mol/L hydrochloric acid solution and/or propylparaben required for the individual formulations were added. During cooling, the previously pre-swollen agents xanthan gum, N-Hance 3196 and/or Carbopol ETD 2020 were added thereto with further stirring. Completion of the swelling process was awaited. Finally, the pH value was adjusted by addition of tartaric acid or monoethanolamine and the agent made up to 100 g with cold water.

2.0 Provision of Agents A2-

The following agents A2 were provided according to Tables 2 and 3:

TABLE 2

| Component | A2a | A2b | A2c | A2d |
|---|---|---|---|---|
| 3,5-Dimethoxy-4-hydroxybenzaldehyde | 10 mmol | — | — | — |
| 3,4,5-Trihydroxybenzaldehyde | — | 10 mmol | — | — |
| 3,4-Dihydroxy-5-methoxybenzaldehyde | — | — | 10 mmol | — |
| 4-Hydroxy-2-methoxybenzaldehyde | — | — | — | 10 mmol |
| Lorol techn. ® | 1.5 | — | 0.5 | — |
| Eumulgin B2 ® | 0.5 | — | 1.5 | — |
| Hydrenol D ® | 3.5 | — | 3.0 | — |
| Cetiol PGL ® | — | 1.0 | — | — |
| Eutanol ® G ® | — | 0.5 | — | 1.0 |
| Cegesoft HF 62 ® | — | — | — | 2.5 |
| Tego Care 450 ® | — | — | — | 0.8 |
| Cutina GMS ® | — | 3.0 | — | — |
| Eumulgin VL 75 ® | — | 0.8 | — | 0.4 |
| Protelan MST 35 ® | — | 0.5 | — | — |
| Plantacare 1200 UP ® | — | — | — | 1.0 |
| Tego Betain 810 ® | — | 1.5 | — | — |
| Rewoteric AM C ® | — | — | — | 2.0 |
| Texapon ALS Benz. ® | — | — | — | 1.5 |
| Dehyton K Cos ® | — | 1.0 | — | — |
| Lamesoft PO 65 ® | — | 1.5 | — | — |
| Cosmedia Guar C 261 ® | — | 0.50 | — | — |
| Xanthan gum | — | — | — | 0.50 |
| Alginat ® | — | — | — | 1.0 |
| Tagat S ® | 1.0 | — | — | — |
| Coconut fatty acid diethanolamine C12-18 | — | — | 2.5 | — |
| Tensianol HK-2 ® | 3.0 | — | — | — |
| Hostapon SCI 85G ® | — | — | 1.5 | — |
| Ethoxydiglycol | 1.0 | — | 0.5 | — |
| Triethanolamine | — | — | 2.0 | — |
| Propylene carbonate | 2.5 | — | 0.5 | — |
| Glycerol | 1.0 | 1.5 | — | 3.0 |
| Ethanol | — | 5.0 | 1.0 | 2.0 |
| Mikrokill ® | 0.3 | — | 0.5 | — |
| Eusolex 232 ® | 0.6 | — | — | — |
| Benzophenone-4 | — | — | 0.8 | — |
| Perfume | 0.10 | — | 0.15 | — |
| Dermosoft 750 ® | — | 0.20 | — | 0.25 |
| Acetic acid | 0.25 | — | — | — |
| Sodium acetate | 0.15 | — | — | — |
| Tartaric acid | Ad pH | Ad pH | Ad pH | Ad pH |
| Water | Ad 100 | Ad 100 | Ad 100 | Ad 100 |

TABLE 3

| Component | A2e | A2f | A2g | A2h |
|---|---|---|---|---|
| 2,3-Dihydro-1,5-dimethyl-3-oxo-2-phenyl-1H- | 10 mmol | — | — | — |
| 2,4-Dimethoxybenzaldehyde | — | 10 mmol | — | — |
| 2-Formyl-1-methyl-quinolinium p-toluenesulfonate | — | — | 10 mmol | — |
| 4-Formyl-1-methyl-quinolinium p-toluenesulfonate | — | — | — | 10 mmol |
| Lorol techn. ® | 1.5 | 2.0 | 0.5 | 1.0 |
| Eumulgin B3 ® | 0.5 | 1.0 | 1.5 | 1.0 |
| Hydrenol D ® | 3.5 | 2.5 | 2.0 | 2.0 |
| Carbopol 940 ® | 0.5 | — | — | 1.5 |
| Polygel W400 ® | — | 1.35 | — | — |
| Walocel HM 4000 PA2910 ® | 0.2 | — | 0.95 | 0.2 |
| Soft CAT ™ Polymer SL-5 ® | 1.0 | — | — | 0.5 |
| Tego Betain BL215 ® | — | 2.5 | — | — |
| Quartamin BTC-131 ® | 2.0 | — | — | 1.0 |
| Crodazosoft DBQ ® | — | — | 1.5 | — |
| Cocoamidopropyl betaine 40% | — | 3.0 | — | 0.5 |
| Protelan AGL 95 ® | — | — | 3.0 | 0.5 |
| Dow Corning 939 ® | 3.0 | — | 0.5 | — |
| Solan ELD ® | — | — | — | 2.0 |
| Abil Soft AF 100 ® | — | 2.5 | 0.5 | — |
| Glycerol | — | 0.8 | — | 1.5 |
| Tween 80 ® | 2.0 | 1.0 | — | — |
| Glycerol carbonate | 1.0 | — | 1.5 | — |
| Benzyl alcohol | — | — | 2.5 | 0.8 |
| Parsol SLX ® | 0.3 | — | — | 0.15 |
| Uvinul T 150 ® | — | 0.3 | — | 0.10 |
| EDTA | 0.25 | — | 0.6 | — |
| Benzoic acid (German Pharmacopoeia) | — | 0.6 | 0.45 | — |
| Perfume | 0.10 | 0.25 | 0.15 | 0.20 |
| Tartaric acid | Ad pH | Ad pH | Ad pH | Ad pH |
| Water | Ad 100 | Ad 100 | Ad 100 | Ad 100 |

Lorol, Eumulgin B1 or Eumulgin B2, Hydrenol D, Cetiol PGL, Eutenol G, Cegesoft HF 62, Tego Care 450, Cutina GMS and/or Eumulgin VL 75 were melted together at 80° C. The proportions of the components Protelan MST 35, Plantacare 1200 UP, Tego Betain 810, Rewoteric AMC, Texapon ALS Benz., Dehyton K cos, Lamesoft PO 65, Soft CAT Polymer SL-5, Tego Betain BL 215, Quartamin BTC-131, Codazosoft BTQ, cocoamidopropyl betaine 40%, Protelan AGL 95, Tagat S, coconut fatty acid diethanolamine C12-18, Tensianol HK-2 and/or Hostapon SCI 85 G required for the individual formulations were incorporated into this melt. The stated proportions of the carbonyl compounds, dissolved in water at a temperature of 80 to 90° C., were added this mixture. While the mixture slowly cooled to room temperature with stirring, the remaining formulation ingredients Tween 80, Dow Corning 939, Solan ELD, Abil Soft AF 100, glycerol, glycerol carbonate, benzyl alcohol, Parsol SLX, Uvinul T 150, benzoic acid (German Pharmacopoeia), triethanolamine, ethoxydiglycol, propylene carbonate, ethanol, Mikrokill, Eusolex 232, Benzophenone-4, Dermosoft 750, acetic acid, sodium acetate and/or perfume were added. The swelling agents Carbopol 940, Polygel W400, Walocel HM 4000 PA2910, Cosmedia Guar C 261, alginate and/or xanthan gum were preswollen in water and added as per the individual formulation. The pH value was then adjusted by addition of tartaric acid or monoethanolamine. Finally, the agent was made up to 100 g with warm water.

3.0 Provision of Agents A3—

The following agents A3 according to Table 4 were provided by simply mixing the stated ingredients:

TABLE 4

| Agent | Component |
|---|---|
| A3a | 20 g monoethanolamine + 0.61 g Tris + 0.10 g |
| A3b | concentrated ammonia solution in water |
| A3c | 10% sodium hydroxide solution in water |
| A3d | 10% arginine solution in water |
| A3e | 10% potassium hydroxide solution in water |

4.0 Dyeing-

Agents A1 and A2 were intimately mixed in a 1:1 weight ratio to produce the ready-to-use dyeing mixture Immediately thereafter, preparation A3 was added in a quantity such that the pH value of the mixture stated in Table 5 below was reached. The resultant ready-to-use dyeing agent was applied in the ratio 3 g of dye mixture to 1 g of hair (Kerling natural white). After an exposure time of 30 minutes at 32° C., the strands were rinsed with lukewarm water and then dried in a hot stream of air (30 to 40° C.).

TABLE 5

| Shade | Formulation combination | Dyeing pH value |
|---|---|---|
| 1 | A1a/A2a/A3a | 8.5 |
| 2 | A1a/A2d/A3b | 7.5 |
| 3 | A1c/A2d/A3c | 8.4 |
| 4 | A1c/A2b/A3d | 7.8 |
| 5 | A1c/A2c/A3e | 7.9 |
| 6 | A1c/A2e/A3a | 8.0 |
| 7 | A1c/A2f/A3b | 8.2 |
| 8 | A1c/A2g/A3c | 8.1 |
| 9 | A1c/A2h/A3d | 9.5 |
| 10 | A1b/A2a/A3e | 8.3 |
| 11 | A1b/A2d/A3d | 8.7 |
| 12 | A1b/A2b/A3b | 7.7 |
| 13 | A1b/A2c/A3c | 8.6 |
| 14 | A1c/A2a/A3a | 7.6 |
| 15 | A1a/A2g/A3e | 8.0 |
| 16 | A1a/A2h/A3d | 8.8 |

5.0 Provision of Decolorizing Agent B-

The following agents B were provided according to Table 6:

TABLE 6

| Component | B1 | B2 | B3 | B4 | B5 |
|---|---|---|---|---|---|
| Hydrogen peroxide | 3.0 | 6.0 | 12.0 | 3.0 | 3.0 |
| 4-Acetyl-1-methylpyridinium p-toluene-sulfonate | — | — | — | 1.0 | — |
| 3,4-Dihydro-2-methylisoquinolinium p-toluenesulfonate | — | — | — | — | 1.0 |
| Hydrenol D | 3.0 | 1.5 | — | 3.0 | 3.0 |
| Lorol techn. | 1.5 | 1.0 | — | 1.5 | 1.5 |
| Eumulgin B2 | 1.0 | — | — | 1.0 | 1.0 |
| N-Hance 3196 | — | — | 1.10 | — | — |
| Jaguar C-17 | — | 0.75 | 0.75 | — | — |
| Texapon NSO | 2.5 | 3.0 | 2.0 | 2.5 | 2.0 |
| Turpinal SL | 1.1 | 1.5 | 1.8 | 1.4 | 1.6 |
| Dipicolinic acid | 0.05 | 0.10 | 0.15 | 0.10 | 0.10 |
| Disodium pyrophosphate | 0.03 | 0.02 | 0.04 | 0.03 | 0.02 |
| Sulfuric acid/sodium hydroxide solution | Ad pH 1.5 | Ad pH 2.6 | Ad pH 4.2 | Ad pH 3.8 | Ad pH 3.1 |
| Water | | | Ad 100 | | |

Lorol, Eumulgin B2 and/or Hydrenol D were melted together at 80° C. Texapon NSO was incorporated into this melt and stirred with a small proportion of water to yield a warm cream. During cooling, hydrogen peroxide, 4-acetyl-1-methylpyridinium p-toluenesulfonate and/or 3,4-dihydro-2-methylisoquinolinium p-toluenesulfonate, the previously preswollen agents Jaguar C-17 and/or N-Hance 3196 and the agents Turpinal SL, dipicolinic acid and/or disodium pyrophosphate were added. The pH value was then adjusted by addition of sulfuric acid or sodium hydroxide solution. Finally, the agent was made up to 100 g with cold water.

6.0 Decolorization and Colorimetric Measurements—

One day after the dyeing procedure, the CIE-Lab values of the dyed strands of hair were determined using a Texaflash DC 3881 instrument from Datacolor. The strands of hair were decolorized by being thoroughly moistened with one of the decolorizing agents B (see Tables 7 and 8). The liquor ratio was 3:1 (decolorizing agent:hair). The pH value of the application mixture was adjusted to the pH value stated in Tables 7 and 8 with agent A3c. The decolorizing agent B was rinsed off the hair after the exposure time at 32° C. stated in Tables 7 or 8. The hair was then dried in a warm stream of air (30 to 40° C.) and colorimetrically measured using the Texaflash DC 3881 instrument from Datacolor for determining CIE-Lab values.

6.1 Calculation of Decolorization Color Differences—

Color differences between the dyed and the decolorized strands of hair are obtained from the respective CIE-Lab values using the color distance formula shown below (see also DIN 6174, German Standards, Beuth Verlag GmbH, Berlin, 1975).

$$\Delta E = [(\Delta L)^2 + (\Delta a)^2 + (\Delta b)^2]^{1/2} \quad \text{(color distance formula)}$$

Tables 7 and 8 summarize the measured CIE-Lab values and the calculated color distance of the dyeing-decolorizing tests according to the invention in accordance with the method according to the invention. The larger is the ΔE value, the better is the decolorization result.

TABLE 7

| | Decolorization | pH value | ET* | dE* | L* | a* | b* | C* | h* |
|---|---|---|---|---|---|---|---|---|---|
| none | none | — | — | — | 75.01 | 2.13 | 21.73 | 21.84 | 84.30 |
| Shade 3 | none | — | — | — | 23.26 | 24.02 | 11.60 | 26.68 | 25.65 |
| Shade 3 | B1 | 4.0 | 20 | 23.67 | 33.44 | 32.19 | 26.60 | 41.76 | 39.57 |
| | | 4.0 | 30 | 24.42 | 35.37 | 32.44 | 27.81 | 42.73 | 40.61 |
| Shade 3 | B2 | 3.8 | 10 | 20.79 | 33.18 | 31.83 | 25.99 | 41.09 | 39.23 |
| | | 3.8 | 20 | 27.34 | 38.61 | 32.21 | 28.78 | 43.20 | 41.78 |
| | | 3.8 | 30 | 26.81 | 40.43 | 30.28 | 28.86 | 41.84 | 43.63 |
| Shade 3 | B3 | 4.2 | 10 | 23.69 | 38.74 | 32.84 | 30.66 | 44.92 | 43.03 |
| | | 4.2 | 20 | 26.74 | 44.40 | 28.77 | 28.47 | 40.48 | 44.69 |
| Shade 3 | B4 | 3.9 | 20 | 15.59 | 35.80 | 32.11 | 25.71 | 41.13 | 38.68 |
| | | 3.9 | 30 | 17.33 | 36.09 | 31.77 | 26.27 | 41.22 | 39.60 |
| Shade 3 | B5 | 4.1 | 20 | 16.03 | 34.01 | 32.16 | 24.83 | 40.63 | 37.66 |
| | | 4.1 | 30 | 17.50 | 34.92 | 31.71 | 24.74 | 40.22 | 37.95 |

*ET = exposure time to decolorizing agent B

TABLE 8

| Shade | | dE* | L* | a* | b* | C* | h* |
|---|---|---|---|---|---|---|---|
| 1 | colored | — | 19.92 | 3.44 | 0.64 | 3.49 | 10.50 |
| | decolorized with B1 at pH 4.2 | 27.92 | 42.04 | 7.08 | 17.29 | 18.68 | 67.73 |
| 2 | colored | — | 27.18 | 30.78 | 17.78 | 35.54 | 30.02 |
| | decolorized with B1 at pH 4.1 | 18.24 | 40.03 | 32.99 | 30.54 | 44.96 | 42.79 |
| 3 | colored | — | 23.71 | 27.22 | 13.65 | 30.45 | 26.62 |
| | decolorized with B1 at pH 4.0 | 14.88 | 33.53 | 31.49 | 23.98 | 39.58 | 37.29 |
| 4 | colored | — | 16.71 | 1.52 | 0.41 | 1.57 | 14.90 |
| | decolorized with B1 at pH 3.9 | 11.38 | 26.23 | 2.90 | 6.49 | 7.10 | 65.94 |
| 5 | colored | — | 16.38 | 2.19 | 0.50 | 2.24 | 12.93 |
| | decolorized with B1 at pH 3.8 | 12.90 | 27.19 | 5.09 | 6.92 | 8.59 | 53.65 |
| 6 | colored | — | 61.81 | 13.50 | 58.75 | 60.28 | 77.00 |
| | decolorized with B1 at pH 3.7 | 12.99 | 66.57 | 10.51 | 47.04 | 48.20 | 77.41 |
| 7 | colored | — | 45.55 | 32.97 | 46.01 | 56.60 | 54.37 |
| | decolorized with B1 at pH 4.3 | 20.20 | 56.41 | 19.36 | 35.76 | 40.66 | 61.58 |
| 8 | colored | — | 25.68 | 7.71 | 20.7 | 7.98 | 15.01 |
| | decolorized with B1 at pH 3.8 | 11.38 | 35.70 | 11.79 | 5.59 | 13.05 | 25.36 |
| 9 | colored | — | 36.02 | 9.86 | 13.38 | 16.62 | 53.61 |
| | decolorized with B1 at pH 3.9 | 11.73 | 45.28 | 10.92 | 20.50 | 23.22 | 61.95 |
| 10 | colored | — | 65.35 | 10.15 | 59.92 | 60.77 | 80.38 |
| | decolorized with B1 at pH 4.0 | 11.81 | 68.89 | 5.90 | 49.49 | 49.84 | 83.20 |
| 11 | colored | — | 66.70 | 0.11 | 51.12 | 51.12 | 89.87 |
| | decolorized with B1 at pH 4.1 | 2.83 | 68.17 | −1.94 | 52.40 | 52.44 | 92.12 |
| 12 | colored | — | 63.68 | 8.83 | 56.44 | 57.12 | 81.11 |
| | decolorized with B1 at pH 4.2 | 10.62 | 66.52 | 4.82 | 47.02 | 84.15 | 10.62 |
| 3 | colored | — | 25.70 | 29.04 | 15.48 | 32.91 | 28.06 |
| | decolorized with B1 at pH 6.8 | 3.95 | 29.39 | 30.07 | 16.45 | 34.27 | 28.69 |
| | colored | — | 23.53 | 26.61 | 12.80 | 29.53 | 25.70 |
| | decolorized with B1 at pH 9.9 | 35.26 | 56.47 | 14.89 | 8.29 | 17.04 | 29.11 |
| | colored | — | 23.04 | 25.18 | 11.54 | 27.70 | 24.60 |
| | decolorized with B4 at pH 10.0 | 31.36 | 51.59 | 15.40 | 20.04 | 25.28 | 52.46 |
| | colored | — | 25.04 | 28.72 | 14.71 | 32.27 | 27.12 |
| | decolorized with B5 at pH 10.1 | 26.27 | 50.10 | 21.98 | 10.61 | 24.41 | 25.77 |
| 14 | colored | — | 19.20 | 2.38 | −4.92 | 5.47 | 295.83 |
| | decolorized with B1 at pH 6.8 | 42.20 | 56.84 | 3.32 | 14.13 | 14.52 | 76.79 |
| | colored | — | 17.89 | 2.54 | −3.92 | 4.67 | 303.01 |
| | decolorized with B1 at pH 9.9 | 52.17 | 63.87 | −0.96 | 20.48 | 20.50 | 92.67 |
| | colored | — | 18.20 | 2.42 | −3.23 | 4.04 | 306.90 |
| | decolorized with B4 at pH 10.0 | 49.81 | 60.70 | 1.36 | 22.72 | 22.76 | 86.58 |
| | colored | — | 18.01 | 2.40 | −3.39 | 4.16 | 305.35 |
| | decolorized with B5 at pH 10.1 | 50.15 | 63.62 | −1.78 | 17.01 | 17.11 | 95.97 |
| 5 | colored | — | 16.79 | 1.86 | −0.93 | 2.08 | 333.59 |
| | decolorized with B1 at pH 7.0 | 19.95 | 36.60 | 0.91 | 1.26 | 1.55 | 54.21 |
| | colored | — | 16.78 | 2.28 | −1.44 | 2.70 | 327.70 |
| | decolorized with B1 at pH 10.0 | 29.68 | 45.14 | 5.18 | 6.80 | 8.55 | 52.72 |
| 6 | colored | — | 66.97 | 8.36 | 53.21 | 53.86 | 81.07 |
| | decolorized with B1 at pH 7.3 | 5.30 | 70.83 | 7.81 | 49.62 | 50.23 | 81.06 |
| | colored | — | 63.45 | 8.70 | 50.42 | 51.16 | 80.21 |
| | decolorized with B1 at pH 10.2 | 28.47 | 72.28 | 2.23 | 24.13 | 24.23 | 84.71 |
| 7 | colored | — | 43.11 | 34.00 | 42.54 | 54.46 | 51.37 |
| | decolorized with B1 at pH 7.0 | 16.12 | 54.28 | 22.38 | 43.00 | 48.48 | 62.51 |
| | colored | — | 43.99 | 31.73 | 43.57 | 53.90 | 53.94 |
| | decolorized with B1 at pH 9.8 | 41.82 | 69.89 | 4.16 | 25.75 | 26.08 | 80.83 |
| 15 | colored | — | 31.67 | 8.84 | 8.61 | 12.34 | 44.26 |
| | decolorized with B1 at pH 7.5 | 9.05 | 40.56 | 10.35 | 9.36 | 13.95 | 42.13 |
| | colored | — | 31.75 | 9.02 | 8.49 | 12.38 | 43.27 |
| | decolorized with B1 at pH 10.5 | 21.52 | 53.17 | 7.91 | 6.76 | 10.41 | 40.51 |

TABLE 8-continued

| Shade | | dE* | L* | a* | b* | C* | h* |
|---|---|---|---|---|---|---|---|
| 16 | colored | — | 40.22 | 12.77 | 18.52 | 22.50 | 55.41 |
|  | decolorized with B1 at pH 6.5 | 14.88 | 52.92 | 10.75 | 26.02 | 28.15 | 67.55 |
|  | colored | — | 43.28 | 13.09 | 18.12 | 22.35 | 54.14 |
|  | decolorized with B1 at pH 10.3 | 21.02 | 61.63 | 6.90 | 26.27 | 27.16 | 75.29 |
| 13 | colored | — | 46.66 | 15.68 | 45.80 | 48.41 | 71.10 |
|  | decolorized with B1 at pH 6.7 | 2.81 | 49.07 | 16.07 | 47.19 | 49.85 | 71.19 |
|  | colored | — | 46.16 | 16.99 | 47.10 | 50.07 | 70.16 |
|  | decolorized with B1 at pH 9.7 | 9.31 | 44.62 | 25.98 | 49.00 | 55.46 | 62.07 |

*exposure time to decolorizing agent B of 20 min 7.0 List of Raw Materials Used—

Abil Soft® AF 100 neutralized polyether/aminosiloxane (INCI name: Methoxy PEG/PPG-7/3 Aminopropyl Dimethicone) (Evonik Degussa)

Carbopol® 940 polyacrylic acid (INCI name: Carbomer) (Noveon) Carbopol® ETD 2020 crosslinked acrylic acid copolymer, white powder (INCI name: Acrylates/C10-30 Alkylacrylate Crosspolymer) (Noveon)

Cegesoft®HF 62 INCI name: Hydrogenated Vegetable Oil (Cognis)

Cetiol® PGL INCI name: Hexyldecanol, Hexyldecyl Laurate (Cognis)

Cosmedia Guar® C 261 guar hydroxypropyltrimethylammonium chloride (at least 93% solids; INCI name: Guar Hydroxypropyltrimonium Chloride) (Cognis Corporation Cosmedia)

Crodazosoft® DBQ INCI name: Quaternium-91, Cetrimonium Methosulfate, Cetearyl Alcohol (approx. 70 wt. % cationic active substance)

Cutina® GMS glyceryl monostearate (max. 2% water; INCI name: Glyceryl Stearate) (Cognis)

Dehyton® K N,N-dimethyl-N-($C_8$-18-cocoamidopropyl) ammonium acetobetaine (approx. 30% active substance; INCI name: Aqua (Water), Cocamidopropyl Betaine) (Cognis)

Dermosoft® 750 INCI name: Perfume (Geranic Acid) (Dr. Straetmanns Chemische Produkte)

Eumulgin® B2 cetylstearyl alcohol with approx. 20 EO units (INCI name: Ceteareth-20) (Cognis)

Eumulgin® B3 cetylstearyl alcohol with approx. 30 EO units (INCI name: Ceteareth-30) (Cognis)

Eumulgin® VL 75 mixture of 20-40 wt. % lauryl glucoside, 20-40 wt. % polyglyceryl-2 dipolyhydroxystearate, 10-30 wt. % glycerol and 10-30 wt. % water (INCI name: Lauryl Glucoside, Polyglyceryl-2 Dipolyhydroxystearate, Glycerin) (Cognis)

Eusolex® 232 2-phenylbenzimidazole-5-sulfonic acid (INCI name: Phenylbenzimidazole Sulfonic Acid) (Merck)

Eutanol® G 2-octyldodecyl alcohol (INCI name: Octyldodecanol) (Cognis)

Hostapon® SCI 85 G sodium cocoylisethionate (at least 84 wt. % active substance, 5-10 wt. % free fatty acid, at most 4 wt. % sodium isethionate; INCI name: Sodium Cocoyl Isethionate) (Clariant)

Hydrenol® D C16-18-fatty alcohol (INCI name: Cetearyl Alcohol) (Cognis)

Jaguar® C 17 guar 2-hydroxy-3-trimethylammoniopropyl ether chloride (INCI name: Guar Hydroxypropyltrimonium Chloride) (Rhodia)

Lamesoft® PO 65 alkyl polyglucoside oleic acid monoglyceride mixture (approx. 65-70% solids; INCI name: Coco-Glucoside, Glyceryl Oleate, Aqua (Water)) (Cognis)

Lorol® techn. $C_{12-18}$ fatty alcohol (INCI name: Coconut Alcohol) (Cognis) Mikrokill® INCI name: Polyaminopropyl Biguanide (S&D Chesham)

N-Hance® 3196 guar 2-hydroxy-3-trimethylammoniopropyl ether chloride (INCI name: Guar Hydroxypropyltrimonium Chloride) (Hercules)

Parsol® SLX dimethicodiethylbenzal malonate (INCI name: Polysilicone-15, CAS No.: 207574-74-1) (DSM Nutritional Products)

Plantacare® 1200 UP $C_{12-16}$ fatty alcohol 1,4-glucoside (approx. 50-53% active substance content; INCI name: Lauryl Glucoside, Aqua (Water)) (Cognis)

Polygel® W400 copolymer of ethyl acrylate and methacrylic acid in aqueous emulsion (29-31 wt. % active substance, INCI name: Acrylates Copolymer) (3V Sigma)

Protelan® AGL 95 sodium dodecylglutamate (aqueous solution with approx. 33 wt. % active substance, INCI name: Sodium Lauroyl Glutamate) (Zschinnmer & Schwarz)

Protelan® MST 35 mixture of sodium N-myristoylsarcosinate and sodium N-methyl-N-cocoyltaurate (40 wt. % active substance, Zschimmer & Schwarz)

Quartamin® BTC-131 approx. 50% QAC, INCI name: Behenoyl PG-Trimonium Chloride (Kao)

Rewoteric® AM C sodium cocoamphoacetate (approx. 30 wt. % active substance, INCI name: Sodium Cocoamphoacetate) (Evonik Degussa)

Soft CAT Polymer SL-5® cellulose with 2-hydroxyethyl ether groups, 2-[2-hydroxy-3-(trimmethylammonio) propoxy]ethyl ether groups and 2-hydroxy-3-(trimethylammmonio)propyl ether groups, counterion is chloride (solid, active substance approx. 91 wt. %, INCI name: Polyquaternium-67) (Amerchol (Dow))

Tagat S® ethoxylated glyceryl monostearate (waxy (melting range 15-25° C.), HLB 16.4, INCI name: PEG-30 Glyceryl Stearate) (Evonik Degussa)

Tego Betain® 801 ($C_8$-$C_{10}$) fatty acid amidopropyl betaine (active substance approx. 35 wt. %, INCI name: Capryl/Capramidopropyl Betaine) (Goldschmidt)

Tego Betain® BL 215 N,N-dimethyl-N-(cocosalkylamidopropyl)ammonium acetobetaine (active substance approx. 30 wt. %, INCI name: Cocamidopropyl Betaine) (Goldschmidt)

Tego Care® 450 stearyl glucoside (HLB 11, INCI name: Polyglyceryl-3 Methylglucose Distearate) (Goldschmidt)

Texapon ALS Benz. ammonium ($C_{12}$-$C_{16}$) fatty alcohol sulfate (27-28 wt. % active substance, INCI name: Ammonium Lauryl Sulfate) (Cognis)

Texapon® NSQ lauryl ether sulfate, sodium salt (approx. 27.5% active substance; INCI name: Sodium Laureth Sulfate) (Cognis)

Turpinal® SL 1-hydroxyethane-1,1-diphosphonic acid (approx. 58-61% active substance content; INCI name: Etidronic Acid, Aqua (Water)) (Solutia)

Tween® 80 sorbitan monooleate with approx. 20 EO units (max. 3 wt. % water; INCI name: Polysorbate-80) (Croda)

Uvinul® T 150 2,4,6-trianilino-p-(carbo-2'-ethylhexyl-1'-oxy)-1,3,5-triazine (INCI name: Ethylhexyl Triazone) (BASF)

Walocel® HM 4000 PA2910 INCI name: Hydroxypropyl Methylcellulose (7-12% hydroxypropoxy groups, 28-30% methoxy groups) (Dow)

We claim:

1. Kit for dyeing and decolorizing keratin-containing fibers comprising:
at least one cosmetic multicomponent dyeing agent having at least one cosmetic agent A1 and at least one cosmetic agent A2,
and at least one cosmetic decolorizing agent B comprising hydrogen peroxide in a cosmetic carrier, and
optionally at least one set of instructions,
wherein the at least one agent A1 and at least one agent A2 are mixed to yield a ready-to-use dyeing agent for dyeing keratin-containing fibers,
wherein the ready-to-use dyeing agent contains at least one CH-acidic compound and at least one reactive carbonyl compound in a cosmetic carrier, and
wherein keratin-containing fibers dyed with the ready-to-use dyeing agent can be decolorized with the decolorizing agent B,
with the proviso that agents A1, A2 and B are present in separately formulated form, wherein the CH-acidic compound is choked from at least one compound of formula (CH-1) and/or at least one compound of formula (CH-2),

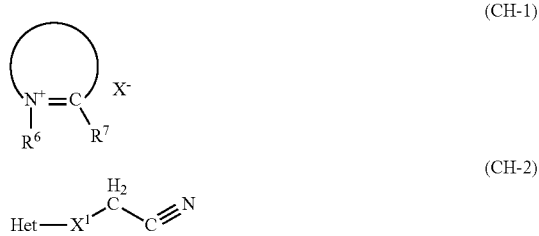

wherein
$R^6$ is a linear or cyclic ($C_1$ to $C_6$) alkyl group, a ($C_2$ to $C_6$)alkenyl group, an optionally substituted aryl group, an optionally substituted heteroaryl group, an aryl-($C_1$ to $C_6$)-alkyl group, a ($C_1$ to $C_6$) hydroxyalkyl group, a ($C_2$ to $C_6$) polyhydroxyalkyl group, a ($C_1$ to $C_6$)-alkoxy-($C_1$ to $C_6$)-alkyl group, a group $R^I R^{II} N—(CH_2)_m—$, wherein $R^I$ and $R^{II}$ mutually independently are a hydrogen atom, a ($C_1$ to $C_6$) alkyl group, a ($C^1$ to $C^4$)hydroxyalkyl group or an aryl-($C_1$ to $C_6$)-alkyl group, wherein $R^I$ and $R^{II}$ together with the nitrogen atom can from a 5-, 6- or 7-membered ring, and m is 2, 3, 4, 5, or 6,
$R^7$ is a($C_1$ to $C_6$)alkyl group,
X is a physiologically acceptable anion,
the cycle of formula (CH-1 is a ring structure comprising heteroatoms and capable of bearing additional substituents,
Het is an optionally substituted heteroaromatic, and
$X^1$ is a direct bond or a carbonl bony group.

2. Kit according to claim 1, wherein the CH-acidic compound is chosen from 2-(2-furoyl)-acetonitrile, 2-(5-bromo-2-furoyl)-acetonitrile, 3-(2,5-dimethyl-3-furyl)-3-oxopropanenitrile, 2-(2-thenyl)-acetonitrile, 2-(3-thenoyl)-acetonitrile, 2-(5-fluoro-2-thenyl)-acetonitrile, 2-(5-chloro-2-thenyl)-acetonitrile, 2-(5-bromo-2-thenyl)-acetonitrile, 2-(5-methyl-2-thenoyl)-acetonitrile, 2-(2,5-dimethylpyrrol-3-oyl)-acetonitrile, 2-(1,2,5-trimethylpyrrol-3-oyl)-acetonitrile, 1H-benzimidazol-2-ylacetonitrile, 1H-benzothiazol-2-ylacetonitrile, 2-(pyrid-2-yl)-acetonitrile, 2,6-bis(cyanomethyl)-pyridine, 2-(indol-3-oyl)-acetonitrile, 2-(2-methylindol-3-oyl)-acetonitrile, 2-(6-hydroxy-4,7-dimethoxy-1-benzofuran-5-oyl)-acetonitrile and the salts with a physiologically acceptable counterion $X^-$ of 1,2-dihydro-1,3,4,6-tetramethyl-2-oxopyrimidinium, 1,2-dihydro-1,3-diethyl-4,6-dimethyl-2-oxopyrimidinium, 1,2-dihydro-1,3-dipropyl-4,6-dimethyl-2-oxopyrimidinium, 1,2-dihydro-1,3-di(2-hydroxyethyl)-4,6-dimethyl-2-oxopyrimidinium, 1,2-dihydro-1,3-diphenyl-4,6-dimethyl-2-oxopyrimidinium, 1,2-dihydro-1,3,4-trimethyl-2-oxopyrimidinium, 1,2-dihydro-1,3-diethyl-4-methyl-2-oxopyrimidinium, 1,2-dihydro-1,3-dipropyl-4-methyl-2-oxopyrimidinium, 1,2-dihydro-1,3-di(2-hydroxyethyl)-4-methyl-2-oxopyrimidinium, 1,2-dihydro-1,3-diphenyl-4-methyl-2-oxopyrimidinium, 1-allyl-1,2-dihydro-3,4,6-trimethyl-2-oxopyrimidinium, 1,2-dihydro-1-(2-hydroxyethyl)-3,4,6-trimethyl-2-oxopyrimidinium, 1,2-dihydro-1,3,4,6-tetramethyl-2-thioxopyrimidinium, 1,2-dihydro-1,3-diethyl-4,6-dimethyl-2-thioxopyrimidinium, 1,2-dihydro-1,3-dipropyl-4,6-dimethyl-2-thioxopyrimidinium, 1,2-dihydro-1,3-di(2-hydroxyethyl)-4,6-dimethyl-2-thioxopyrimidinium, 1,2-dihydro-1,3-diphenyl-4,6-dimethyl-2-thioxopyrimidinium, 1,2-dihydro-1,3,4-trimethyl-2-thioxopyrimidinium, 1,2-dihydro-1,3-diethyl-4-methyl-2-thioxopyrimidinium, 1,2-dihydro-1,3-dipropyl-4-methyl-2-thioxopyrimidinium, 1,2-dihydro-1,3-di(2-hydroxyethyl)-4-methyl-2-thioxopyrimidinium, 1,2-dihydro-1,3-diphenyl-4-methyl-2-thioxopyrimidinium, 1,2-dihydro-3,4-dimethyl-2-oxoquinazolinium, 1,2-dihydro-3,4-dimethyl-2-thioxoquinazolinium and mixtures thereof.

3. Kit according to claim 1, wherein the reactive carbonyl compound is chosen from benzaldehyde and derivatives thereof, naphthaldehyde and derivatives thereof, cinnamaldehyde and derivatives thereof, 2-formylmethylene-1,3,3-trimethylindoline (Fischer's aldehyde or tribasic aldehyde), 2-indolealdehyde, 3-indolealdehyde, 1-methylindole-3-aldehyde, 2-methylindole-3-aldehyde, 2-(1',3',3'-trimethyl-2-indolinylidene)-acetaldehyde, 1-methylpyrrole-2-aldehyde, pyridoxal, 2,3-dihydro-1,5-dimethyl-3-oxo-2-phenyl-1H-pyrazole-4-carboxaldehyde, furfural, 5-nitrofurfural, chromone-3-aldehyde, 3-(5'-nitro-2'-furyl)-acrolein, 3-(2'-furyl)-acrolein and imidazole-2-aldehyde, 5-(4-dimethyl-aminophenyl)penta-2,4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 5-(4-dimethylamino-1-naphthyl)penta-3,5-dienal, piperonal, 6-nitropiperonal, 2-nitropiperonal, 5-nitrovanillin, 2,5-dinitrosalicylaldehyde, 5-bromo-3-nitrosalicylaldehyde, 3-nitro-4-formylbenzenesulfonic acid, 4-formyl-1-methylpyridinium, 2-formyl-1-methylpyridinium, 4-formyl-1-ethylpyridinium, 2-formyl-1-ethylpyridinium, 4-formyl-1-benzylpyridinium, 2-formyl-1-benzylpyridinium, 4-formyl-1,2-dimethylpyridinium, 4-formyl-1,3-dimethylpyridinium, 4-formyl-1-methylquinolinium, 2-formyl-1- methylquinolinium, 5-formyl-1-methylquinolinium, 6-formyl-1-methylquinolinium, 7-formyl-1-methylquinolinium, 8-formyl-1-methylquinolinium, 5-formyl-1-ethylquinolinium, 6-formyl-1-ethylquinolinium, 7-formyl-1-ethylquinolinium, 8-formyl-1-ethylquinolinium, 5-formyl-1-benzylquinolinium, 6-formyl-1-benzylquinolinium, 7-formyl-1-benzylquinolinium, 8-formyl-1-benzylquinolinium, 5-formyl-1-allylquinolinium, 6-formyl-1-allylquinolinium, 7-formyl-1-allylquinolinium and 8-formyl-1-allylquinolinium benzenesulfonate, p-toluenesulfonate, methanesulfonate, perchlorate, sulfate, chloride, bromide, iodide, tetrachlorozincate, methylsulfate, trifluoromethanesulfonate, tetrafluoroborate, isatin, 1-methylisatin, 1-allylisatin, 1-hydroxymethylisatin, 5-chloroisatin, 5-methoxyisatin, 5-nitroisatin, 6-nitroisatin, 5-sulfoisatin, 5-carboxyisatin, quinisatin, 1-methylquinisatin, and mixtures thereof.

4. Kit according to claim 1, wherein the ready-to-use dyeing agent contains no oxidation dye precursors.

5. Kit according to claim 1, wherein the hydrogen peroxide is present in the decolorizing agent B in quantities of 0.5 and 12 wt. %, relative to the weight of the entire agent.

6. Kit according to claim 1, wherein the decolorizing agent B has a pH value of 4 to 11.

7. Kit according to claim 1, wherein, apart from hydrogen peroxide, the decolorizing agent B contains no further peroxo compounds.

8. Kit according to claim 1, wherein the decolorizing agent B contains at least one surfactant.

9. Method for decolorizing dyed keratin-containing fibers, comprising:
 dyeing keratin-containing fibers with a dyeing agent containing a combination of at least one CH-acidic compound with at least one reactive carbonyl compound in a cosmetic carrier,
 applying a decolorizing agent comprising hydrogen peroxide in a cosmetic carrier onto the keratin-containing fibers dyed with the dyeing agent,
 leaving the decolorizing agent on the fibers for 1 to 30 minutes, and
 rinsing the decolorizing agent out wherein the CH-acidic compound is chosen from at least one compound of formula (CH-1) and/or at least one compound of formula (CH-2),

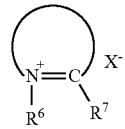
(CH-1)

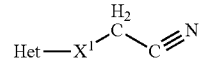
(CH-2)

wherein
$R^6$ is a linear or cyclic ($C_1$ to $C_6$) alkyl group, a ($C_2$ to $C_6$) alkenyl group, an optionally subsituted aryl group, an optionally substituted heteroaryl group, an aryl-($C_1$ to $C_6$)-alkyl group, a ($C_1$ to $C_6$ hydroxyalkyl group, a ($C_1$ to $C_6$)-alkoxy-($C_1$ $C_6$)-alkyl group, a group $R^I R^{II} N$—$(CH_2)_m$—, wherein $R^I$ and $R^{II}$ mutually independently are a hydrogen atom, a ($C_1$ to $C_4$) alkyl group, a($C_1$ to $C_4$)hydroxyalkyl group or an aryl-($C_1$ to $C_6$)-alkyl group, a ($C_1$ to $C_4$) hydroxyalkyl group or an aryl-($C_1$ to $C_6$)-alkyl group, whererin $R^I$ and $R^{II}$ together with the nitrogen atom can form a 5-, 6- or 7-membered ring, and m is 2,3,4,5 or 6,
$R^7$ is a ($C_1$ to $C_6$)-alkyl group,
X is a physiologically acceptable anion,
the cycle of formula (CH-1)is a ring structure comprising heteroatoms and capable of bearing additional substituents,
Het is an optionally substituted heteroaromatic, and
$X^1$ is a direct bond or a carbonyl group.

10. Method according to claim 9, wherein the decolorizing agent comprises hydrogen peroxide in amounts of from 0 to 12 wt. %, based on the weight of the entire agent.

11. Method according to claim 9, wherein the decolorizing agent is left on the fibers for 5 to 20 minutes.

12. Method according to claim 10, wherein the decolorizing agent contains no organic peroxo compounds and no inorganic per-salts.

* * * * *